United States Patent
Aliper et al.

(10) Patent No.: US 12,307,379 B2
(45) Date of Patent: *May 20, 2025

(54) SUBSET CONDITIONING USING VARIATIONAL AUTOENCODER WITH A LEARNABLE TENSOR TRAIN INDUCED PRIOR

(71) Applicant: INSILICO MEDICINE IP LIMITED, Hong Kong (HK)

(72) Inventors: Aleksandr Aliper, Abu Dhabi (AE); Aleksandrs Zavoronkovs, Abu Dhabi (AE); Alexander Zhebrak, Abu Dhabi (AE); Daniil Polykovskiy, Montréal (CA); Maksim Kuznetsov, Montréal (CA); Yan Ivanenkov, Abu Dhabi (AE); Mark Veselov, Abu Dhabi (AE); Vladimir Aladinskiy, Abu Dhabi (AE); Evgeny Putin, Abu Dhabi (AE); Yuriy Volkov, Abu Dhabi (AE); Arip Asadulaev, Abu Dhabi (AE)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,870

(22) Filed: Dec. 13, 2023

(65) Prior Publication Data
US 2024/0152763 A1    May 9, 2024

Related U.S. Application Data

(63) Continuation of application No. 18/114,566, filed on Feb. 27, 2023, now Pat. No. 11,893,498, which is a
(Continued)

(51) Int. Cl.
*G06N 3/092* (2023.01)
*G06N 3/0455* (2023.01)
(Continued)

(52) U.S. Cl.
CPC .......... *G06N 3/092* (2023.01); *G06N 3/0455* (2023.01); *G06N 3/0475* (2023.01); *G06N 3/084* (2013.01)

(58) Field of Classification Search
CPC .... G06N 3/092; G06N 3/0455; G06N 3/0475; G06N 3/084
(Continued)

(56) References Cited

U.S. PATENT DOCUMENTS

| 2012/0233127 | A1 | 9/2012 | Solmer et al. |
| 2015/0238148 | A1* | 8/2015 | Georgescu ............... G06F 18/28 |
| | | | 600/408 |

(Continued)

FOREIGN PATENT DOCUMENTS

| CN | 108140146 A | 6/2018 |
| CN | 108431834 A | 8/2018 |

OTHER PUBLICATIONS

D. Polykovskiy et al., "Entangled Conditional Adversarial Autoencoder for de Novo Drug Discover", Molecular Pharmaceutics, vol. 15, No. 10, Sep. 4, 2018, pp. 4398-4405. (Year: 2018).*

(Continued)

*Primary Examiner* — Zaihan Jiang
*Assistant Examiner* — Kristin Dobbs
(74) *Attorney, Agent, or Firm* — MASCHOFF BRENNAN

(57) ABSTRACT

The proposed model is a Variational Autoencoder having a learnable prior that is parametrized with a Tensor Train (VAE-TTLP). The VAE-TTLP can be used to generate new objects, such as molecules, that have specific properties and that can have specific biological activity (when a molecule). The VAE-TTLP can be trained in a way with the Tensor
(Continued)

Train so that the provided data may omit one or more properties of the object, and still result in an object with a desired property.

20 Claims, 14 Drawing Sheets

Related U.S. Application Data continuation-in-part of application No. 16/134,624, filed on Sep. 18, 2018, now Pat. No. 11,593,660.

(51) Int. Cl.
*G06N 3/0475* (2023.01)
*G06N 3/084* (2023.01)

(58) Field of Classification Search
USPC .......................................................... 706/25
See application file for complete search history.

(56) References Cited

U.S. PATENT DOCUMENTS

| | | |
|---|---|---|
| 2016/0093048 A1 | 3/2016 | Cheng et al. |
| 2016/0155136 A1 | 6/2016 | Zhang et al. |
| 2017/0161635 A1 | 6/2017 | Oono et al. |
| 2017/0371017 A1 | 12/2017 | Odry et al. |

OTHER PUBLICATIONS

Kuznetsov, M., et al., "Subset-Conditioned Generation Using Variational Autoencoder With A Learnable Tensor-Train Induced Prior," Third workshop on bayesian deep learning, pp. 8 (2018).

International Search Report & Written Opinion of the International Searching Authority Dated Aug. 30, 2019 as received in Application No. PCT/US2019/037989.

Extended European Search Report dated May 31, 2022 issued in EP Application No. 19861711.0, 14 pages.

D. Polykovskiy et al.; "Entangled Conditional Adversarial Autoencoder for de Novo Drug Discovery"; Molecular Pharmaceutics; vol. 15, No. 10; Sep. 4, 2018; pp. 4398-4405; XP055712924; US ISSN: 1543-8384; DOI: 10.1021/acs.molpharmaceut.8b00839.

R.Gomez-Bombarelli et al.; "Automatic Chemical Design using a Data-Driven Continuous Representation of Molecules"; ARXIV. org. Cornell University Library; Oct. 7, 2016; XP081350646; DOI: 10.1021/ACSCENTSCI.7B00572.

O.R. Sharir et al.; "Tensorial Mixture Models"; ARXIV.org; Cornell University Library; Oct. 13, 2016; XP081353311.

Zhao-Yu Han et al.; "Unsupervised Generative Modeling Using Matrix Product States"; ARXIV.org; Cornell University Library; Sep. 6, 2017; XP081327155; DOI: 10.1103/PHYSREVX.8.031012.

E. Putin et al.; "Reinforced Adversarial Neural Computer for de Novo Molecular Design"; Journal of Chemical Information and Modeling; vol. 58, No. 6; May 15, 2018; pp. 1194-1204; XP055714913; US ISSN: 1249-9596; DOI: 10.1021/acs.jcim.7b00690.

China National Intellectual Property Administration; First Office Action issued in CN Application No. 201980074420.5; dated Jan. 2, 2024.

China National Intellectual Property Administration; Second Office Action issued in CN Application No. 201980074420.5; dated Jul. 18, 2024.

Nikolenko, Kaduirin A.; "DruGAN: An Advanced Generative Adversarial Autoencoder Model for de Novo Generation of New Molecules with Desired Molecular Properties in Silico"; Molecular Pharmaceutics, 2017; vol. 14, N0, pp. 3098-3104; http://dx.doi.org/10.1021/acs.molpharmaceut.7b00346.

* cited by examiner

SUBSET CONDITIONING USING VARIATIONAL AUTOENCODER WITH A LEARNABLE TENSOR TRAIN INDUCED PRIOR

CROSS-REFERENCE TO RELATED APPLICATIONS

This patent application is a continuation of U.S. application Ser. No. 18/114,556 filed Feb. 27, 2023, which is a continuation-in-part of U.S. application Ser. No. 16/134,624 filed Sep. 18, 2018 now U.S. Pat. No. 11,593,660, which applications are incorporated herein by specific reference in their entirety.

BACKGROUND

Deep neural networks (DNNs) are computer system architectures that have recently been created for complex data processing and artificial intelligence (AI). DNNs are machine learning models that employ more than one hidden layer of nonlinear computational units to predict outputs for a set of received inputs. DNNs can be provided in various configurations for various purposes, and continue to be developed to improve performance and predictive ability.

It would be advantageous to have a computer method for generating an object that satisfies a condition, where some conditions may be known and where some conditions may not be known using one or more DNNs.

SUMMARY

In some embodiments, a method for training a model to generate an object is provided. The method can include the following steps: providing a model configured as a variational autoencoder with a tensor train; providing a dataset having object data for an object and property data for a property of the object; processing the object data of the dataset to obtain latent object data with an object encoder of the model, wherein the latent object data includes a distribution of latent variables having a mean and a variance; sampling one or more latent variables from the obtained distribution of latent variables; processing the sampled one or more latent variables with defined object properties to compute a probability of the samples having the defined object properties; processing the sampled one or more latent variables through an object decoder to obtain a reconstructed object; determining a reconstruction loss of the reconstructed object from an original object from the object data; computing a Kullback-Leibler divergence from the probability of the samples having the defined object properties; using the determined reconstruction loss and computed Kullback-Leibler divergence to compute a loss from the data set; perform a gradient descent until the reconstructed object is sufficiently representative of the original object and has the defined object properties; obtaining a trained model configured as a trained variational autoencoder with a learnable prior that is parameterized with the tensor train; and providing the trained model.

In some embodiments, the method can further include further training the trained model with reinforced leaning, wherein the reinforced learning produces the reconstructed objects having a defined characteristic. In some aspects, the training of the trained model with the reinforced learning includes: discarding the object encoder; fixing weights of all layers of the object decoder except for a first layer of the object decoder; performing the following steps until convergence: estimate a mean and variance for each dimension of a previously obtained distribution of latent variables, the previously obtained distribution of latent variables being defined as a learnable prior; obtain an exploration latent variable for each dimension from outside of the latent variables produced by the encoder; pass the exploration latent variable through the decoder to obtain a reconstructed object based on the exploration latent variable; compute rewards for the reconstructed object based on at least one defined reward; and apply a single gradient ascent step to maximize a total reward with respect to a parameter of the learned prior and first layer of the decoder.

In some embodiments, a method of generating an object with a desired property can include: obtaining the trained model of one of the embodiments; identify a desired object property; obtaining a latent code from a tensor train distribution conditioned on the desired object property; generating the object with the desired object property with the decoder; and providing the generated object with the desired object property.

In some embodiments, the method may include: obtaining a learnable prior based on the latent code and desired properties and/or the learnable prior entangling the latent code with object properties; obtaining a set of properties; marginalize the learnable prior over a set of properties not in the set of desired properties; conditioning the marginalized learnable prior over properties in the set of desired properties to obtain a distribution over latent space; sampling from the distribution over latent space; and processing the sampled latent vector with a decoder to obtain a generated object with predefined properties. The conditioning can include changing distributions over latent variables to provide objects with desired properties. the Changing of the distributions can be done by the formula: $p(z|properties)=p(z, properties)/p(properties)$.

In some embodiments, a computer program product can include a non-transient, tangible memory device having computer-executable instructions that when executed by a processor, cause performance of a method comprising: providing a model configured as a variational autoencoder with a tensor train, providing a dataset having object data for an object and property data for a property; processing the object data of the dataset to obtain latent object data with an object encoder of the model, wherein the latent object data includes a distribution of latent variables having a mean and a variance; sampling one or more latent variables from the obtained distribution of latent variables; processing the sampled one or more latent variables with defined object properties to compute a probability of the samples having the defined object properties; processing the sampled one or more latent variables through an object decoder to obtain a reconstructed object; determining a reconstruction loss of the reconstructed object from an original object from the object data; computing a Kullback-Leibler divergence from the probability of the samples having the defined object properties; using the determined reconstruction loss and computed Kullback-Leibler divergence to compute a loss from the data set; perform a gradient descent until the reconstructed object is sufficiently representative of the original object and has the defined object properties; obtaining a trained model configured as a trained variational autoencoder with a learnable prior that is parameterized with a tensor train; and providing the trained model.

In some embodiments, the executed method performed by the computer program product further comprises further training the trained model with reinforced leaning, wherein the reinforced learning produces the reconstructed objects having a defined characteristic, wherein the training of the trained model with the reinforced learning includes: discarding the object encoder; fixing weights of all layers of the object decoder except for a first layer of the object decoder; performing the following steps until convergence: estimate a mean and variance for each dimension of a previously obtained latent samples from learnable prior; obtain an exploration latent variable for each dimension from outside of the distribution specified by means and variances obtained on previous step; pass the exploration latent variable through the object decoder to obtain a reconstructed object based on the exploration latent variable; compute rewards for the reconstructed object based on at least one defined reward; and apply a single gradient ascent step to maximize a total reward with respect to a parameter of the learned prior and first layer of the decoder.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
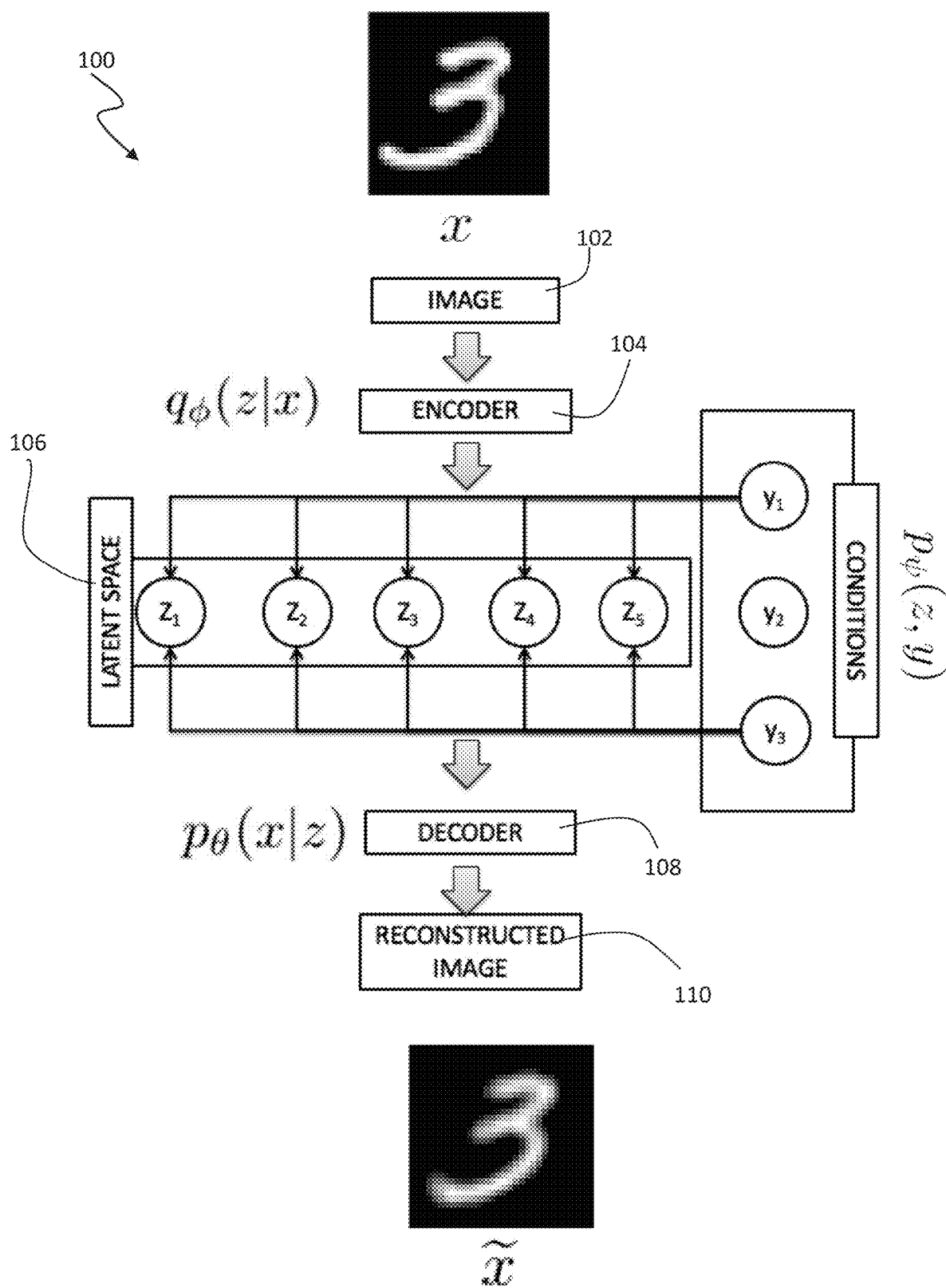
FIG. 1 includes a schematic representation of the architecture of the VAE-TTLP model.

The elements of the figures are arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

An autoencoder (AE) is a type of deep neural network (DNN) used in unsupervised learning for efficient information coding. The purpose of an AE is to learn a representation (e.g., encoding) of objects. An AE contains an encoder part, which is a DNN that transforms the input information from the input layer to the latent representation (e.g., latent code), and includes a decoder part, which uses the latent representation and decodes an original object with the output layer having the same dimensionality as the input for the encoder. Often, a use of an AE is for learning a representation or encoding for a set of data. An AE learns to compress data from the input layer into a short code, and then un-compress that code into something that closely matches the original data. In one example, the original data may be a molecule that interacts with a target protein, and thereby the AE can design a molecule that is not part of an original set of molecules or select a molecule from the original set of molecules or variation or derivative thereof that interacts (e.g., binds with a binding site) of the target protein.

Generative Adversarial Networks (GANs) are structured probabilistic models that can be used to generate data. GANs can be used to generate data (e.g., a molecule) similar to the dataset (e.g., molecular library) GANs are trained on. A GAN can include two separate modules, which are DNN architectures called: (1) discriminator and (2) generator. The discriminator estimates the probability that a generated product comes from the real dataset, by working to compare a generated product to an original example, and is optimized to distinguish a generated product from the original example. The generator outputs generated products based on the original examples. The generator is trained to generate products that are as real as possible compared to an original example. The generator tries to improve its output in the form of a generated product until the discriminator is unable to distinguish the generated product from the real original example. In one example, an original example can be a molecule of a molecular library of molecules that bind with a protein, and the generated product is a molecule that also can bind with the protein, whether the generated product is a variation of a molecule in the molecular library or a combination of molecules thereof or derivatives thereof.

Adversarial Autoencoders (AAEs) are probabilistic AEs that use GANs to perform variational inference. AAEs are DNN-based architectures in which latent representations are forced to follow some prior distribution via the discriminator.

A conditional architecture may be considered a supervised architecture because the processing is supervised by the condition. As such, the conditional architecture may be configured for generating objects that match a specific condition (e.g., property of molecule). In some applications, a conditional model can take values of conditions into account, even if the values of conditions are only partially known. During the generation process, the conditional architecture may only have a few conditions that are specified, and thereby the rest of the conditions can take arbitrary values, at least initially.

A subset conditioning problem is defined as a problem of learning a generative model with partially observed conditions during training and/or generation (active use). The architecture described herein, which can be used for a subset conditioning problem, is a variational autoencoder-based generative model extended for conditional generation and includes a tensor train decomposition that parameterizes its learnable prior, which can be referred to as a VAE-TTLP. The VAE-TTLP can be used to solve a subset conditioning problem by allowing for partially specifying condition values. The VAE-TTLP can be used as a discriminative model to predict any missing and/or unobserved values, and may be trained for any encoder/decoder architecture.

Generally, the present technology relates to conditional generative models that are configured to produce realistic objects (e.g., chemicals, phrases, pictures, audio, etc.) in many domains including chemistry, text, images, video, and audio. However, some applications, for example in the field of chemistry, such as for biomedical applications where the missing data (e.g., property of molecule) is a common issue, require a model that is trained to condition on multiple properties with some of the properties being unknown during the training or generation procedure. As such, the VAE-TTLP is a model that extends a Variational Autoencoder (VAE) by adding a learnable prior (LP), which is parametrized with a Tensor-Train (TT). The architecture VAE-TTLP described herein can also be used to turn any pre-trained autoencoder into a conditional generative model.

The VAE-TTLP can be configured to generate objects with a specific set of properties, where the object can be an image, video, audio, molecules, or other complex objects. The properties of the objects themselves may be complex and some properties may be unknown. In some applications of conditional models, values of properties are only known partially, which now can be used with the VAE-TTLP. The VAE-TTLP can be considered to be a model that undergoes two phase, which are (1) training the model with objects with and without object-specific properties, and then using the trained model to (2) generate objects that are indistinguishable from the objects used to train the model and which also satisfy the properties whether known or unknown. Also, during the generation process using the model, the operator of the model can specify only a few properties, allowing the rest of properties to take arbitrary values. For example, the VAE-TTLP can be particularly useful for reconstructing lost or deteriorated parts of objects, such as lost parts of images, text, or audio. In such cases, a model can be trained to generate full objects (e.g., images) conditioned on observed elements. During the training procedure, the model is provided access to full images, but for the generation, the operator may specify only observed pixels as a condition (e.g., property). The similar problem appears in drug discovery, where the operator uses the model to generate new molecular structures with predefined properties, such as activity against a specific target or a particular solubility. In most cases, the intersection between measured parameters in different studies is usually small, so the combined data from these studies have a lot of missing values. During the generation, the operator might want to specify only the activity of a molecule as a property, so the resulted solubility of generated molecules can initially take an arbitrary value. Here, the process will have missing values in properties during training as well as in generation procedures.

In some embodiments, the object can be any type of object in view of the examples of image, video, audio, text, and molecule. As such, the object can be anything that is represented by data, which can be perceived by human. Accordingly, the object data can include the data that defines that which is perceived by the human. Further examples of the object can include biological data, such as biological data profiles of genomics, transcriptomics, proteomics, metabolomics, lipidomics, glycomics, or secretomics, as well as combinations thereof or others. Any omic biological data signature may be an object. For example, a gene expression profile can be a genomic biological data signature. A protein signature can also be an object that shows the proteomic profile, which can be obtained from a biological sample.

In some embodiments, the object is a molecule, such as a small molecule, macromolecule, polypeptide, protein, antibody, oligonucleotide, nucleic acid (e.g., RNA, DNA, etc.), polypeptide, carbohydrate, lipid, or combinations thereof, whether natural or synthetic.

In some embodiments, the image, video, audio, or text objects can have suitable properties related thereto, such as the content thereof. These types of objects can have properties consistent with the type of information usually present. Images can include scenery that includes common environmental features, whether natural (e.g., sky, earth, plants, animals, etc., or man-made such as buildings, roads, articles of manufacture, and ornamentals. Video can include the properties of images in a sequence of images with or without sounds corresponding to the imagery in the video. Audio can include sounds of any type, from animal sounds, such as human voice, as well as music, and natural environment sounds (e.g., river, ocean, wind, thunder, etc.). Text can include properties of words, phrases, sentences, paragraphs, chapters, and any type of textual language subject matter.

In some embodiments, the property can be biological activity of the object, such as the biological response to the property, which may be a modulation of any of transcriptomic data profile, proteomic data profile, metabolomic data profile, lipidomic data profile, glycomic data profile, or secretomic data profile, as well as combinations thereof or others. Gene expression profiles in response to activity of an object may be an exemplary property. Also, absorption, distribution, metabolism, and excretion (ADME) or any pharmacokinetic data may be properties of an object in an organism, organ, fluid, extracellular matrix, or cell thereof. Toxicity is another example of a biological property. Any modulation of a biological pathway may be considered to be a property of an object. Additionally, the property can be physicochemical properties of the molecule types described herein. The physicochemical properties may also be molecular weight, melting point, boiling point, vapor point, molecular polarity, Henry's phase distribution, and the extrinsic properties of pressure (P) and moles (n), as well as others.

In some aspects, the object may be defined as a property as described herein, and thereby the corresponding property is the object that has that property. This shows the traditional objects and properties can be switched, such that the property is used as an object, and the object is used as a property.

A problem of learning with a generative model with partially observed properties during training and/or generation (e.g., some properties are not known or used during training and/or conditioning) is referred to as a subset conditioning problem. The main contributions of such a subset condition problem by the VAE-TTLP are outlined as follows. The VAE-TTLP is an autoencoder-based generative model with Tensor Train decomposition that parameterizes its learnable prior. The VAE-TTLP is applied to a subset conditioning problem (e.g., with unknown properties), and thereby the model is trained with a partially labeled data set, and then the model is used to generate objects from a few specified properties. The VAE-TTLP is evaluated using known objects (e.g., images or molecules), conditioning the objects on a subset of attributes (e.g., features in images, or properties of a molecule). The VAE-TTLP provided herein can provide suitable generated objects with lower condition violations compared to previously conditional models.

Based on the foregoing, the VAE framework is described with respect to conditional generation. The VAE is a generative autoencoder-like model. The $\phi$-parameterized encoder maps a data point $x \in \mathcal{X}$ into a latent space Z using a distribution $q_\phi(z|x)$. Samples from $q_\phi(z|x)$ are then reconstructed back into an initial data point using the decoder $p_\theta(x|z)$. The model assumes existence of some prior distribution on latent codes $p(z)$ (it can be some complex learnable prior or distribution some standard form, such as standard normal distribution $\mathcal{N}(0,I)$. The model is trained by the maximization of the evidence lower bound:

$$\log p(x) \geq \mathcal{L}_{VAE}(\theta, \phi) = \mathbb{E}_{q(z|x)} \log p_\theta(x|z) - \mathcal{KL}(q_\phi(z|x)\|p(z)) \approx \approx \frac{1}{l} \sum_{i=1}^{l} \log p_\theta(x|z_i) - \mathcal{KL}(q_\phi(z|x)\|p(z)), \quad (1)$$

wherein $z_i \sim q_\phi(z|x)$, and the $\mathcal{KL}$ term is a Kullback-Leibler divergence, which can be either computed analytically, or estimated using Monte Carlo sampling:

$$KL(q_\phi(z|x)\|p(z)) \approx \frac{1}{l} \sum_{i=1}^{l} \log \frac{q_\phi(z|x)}{p(z)}, \quad z_i \sim q_\phi(z|x) \quad (2)$$

To get unbiased estimates of gradients of $\mathcal{L}_{VAE}$, a reparameterization is usually applied, replacing $z_i \sim q_\phi(z|x)$, wherein $z_i \sim g_\theta(x, \epsilon_i), \epsilon_i \sim \mathcal{N}(0,I)$, with a deterministic function $g_\theta$.

The standard VAE with a normal prior $p(z) = \mathcal{N}(z|0,I)$ can be improved by replacing $p(z)$ with a more complex distribution $p_\psi(z)$, which is referred to as a learnable prior. More flexible learnable priors results in a tighter evidence bound and solve a problem of the decoder ignoring latent codes. In the model presented herein, the complex prior distribution $p_\psi(z)$ is parameterized using Tensor Train decomposition and entangled with object properties resulting in $p_\psi(z,y)$. For the task of conditional generation, the model is trained to perform sampling from $p(x|y)$, where y is a given value of the condition. The VAE can be modified for this setting by a conditioning encoder, decoder and prior on y, which results in a following ELBO:

$$\log p(x,y) \geq \mathcal{L}_{CVAE}(\theta,\phi,\psi) = \mathbb{E}_{q_\phi(z|x,y)} \log p_\theta(x|z,y) - \mathcal{K} \mathcal{L}(q_\phi(z|x,y)\|p_\psi(z|y)) + \log p_\psi(y) \quad (3)$$

A Tensor Train (TT) decomposition allows for large high-dimensional tensors to be represented with a relatively small number of parameters. Such decomposition can be useful to store high-dimensional discrete distributions. For example, a joint distribution $p(r_1, r_2, \ldots r_n)$ of n discrete random variables $r_k$ taking values from $\{0, 1, \ldots N_k\}$. This distribution can be represented as a n-dimensional tensor $P[r_1, r_2, \ldots r_n] = p(r_1, r_2, \ldots r_n)$. The number of elements in this tensor grows exponentially with the number of dimensions n. For 50 binary variables, the tensor can contain $2^{50} \approx 10^{15}$ float numbers. To reduce the number of parameters, the TT format approximates tensor P using low-rank matrices $Q_k[r_k] \in \mathbb{R}^{m_k \times m_{k+1}}$ called cores:

$$P[r_1, r_2, \ldots, r_n] \approx 1_{m_1}^T \cdot Q_1[r_1] \cdot Q_2[r_2] \ldots Q_n[r_n] \cdot 1_{m_{n+1}}, \quad (4)$$

where $1_m \in \mathbb{R}^{m \times 1}$ is a column-vector of ones. For each value of a random variable $r_k$, there is selected a specific matrix $Q_k[r_k]$ and then multiply them for all random variables. In this format, the number of parameters grows linearly with the number of dimensions. As the size $m_k$ of cores increases, more complex distributions can be represented in the TT format.

The TT decomposition for discrete distributions allows the model to compute marginal and conditional distributions, as well as sampling from them without computing the whole tensor $P[r_1, r_2, \ldots r_n]$. For example, to marginalize out the random variable $r_k$, the protocol can sum up all values of $Q_k[r_k]$, getting $$\bar{Q}_k = \sum_{r_k=1}^{N_k} Q_k[r_k]:$$

$$P[r_1, \ldots, r_{k-1}, r_{k+1}, \ldots, r_n] = 1_{m_1}^T \cdot \Pi_{j=1}^{k-1} Q_j[r_j] \cdot \bar{Q}_k \cdot \Pi_{j=k+1}^n Q_j[r_j] \cdot 1_{m_{n+1}} \quad (5)$$

Similarly, to get a marginal distribution over a single variable, the protocol can compute:

$$P[r_k] = 1_{m_1}^T \cdot \Pi_{j=1}^{k-1} \bar{Q}_j \cdot Q_k[r_k] \cdot \Pi_{j=k+1}^n \bar{Q}_j \cdot 1_{m_{n+1}} \quad (6)$$

Note that these marginals can be computed in polynomial time, without the need to compute the full distribution. Having marginals, the model can also compute conditionals, as well as a normalizing constant. Finally, sampling can be efficiently performed using the chain rule.

Tensor Ring is a more advanced model that extends TT format. Intuitively, all tensor dimensions should be treated similarly, as there is no explicit meaning covered under their ordering. In TT format, first and last cores $Q_1$ and $Q_n$ are multiplied by the vector of ones. In the Tensor Ring model, the first and the last dimensions are linked together in a similar way as neighboring intermediate cores. The Tensor Ring model multiplies inner cores and then computes the trace of the resulting matrix, getting:

$$P[r_1, r_2, \ldots, r_n] = T_r(Q_1[r_1] \cdot Q_2[r_2] \ldots Q_n[r_n]).$$

This model is called a Tensor Ring because this decomposition is invariant to the cyclic shift of its dimensions (since the trace is cycle-invariant). This approach can approximate more complex distributions with lower core sizes. Also, from the view of computational graphs, information paths in ring tensor format become shorter, which may help learning parameters $Q_k[r_k]$ faster.

To solve a subset conditioning problem, the VAE-TTLP can be used to estimate a joint distribution $p(z, y)$ of latent codes z and conditions y in a Tensor Train format. Having this distribution allows the model to compute the likelihood of partially labeled data points by marginalizing over unobserved values. During generation, the model can sample from conditional distribution over latent codes, given observed conditions (e.g., properties). Now, the Tensor Train format can be used for discrete distributions.

The model can assume the latent codes $z=[z_1, \ldots z_d]$ are continuous while conditions (e.g., properties) $y=[y_1, \ldots y_n]$ are discrete. The goal is to build a Tensor Train representation for a joint distribution $p_\psi(z,y)$ that can model complex dependencies between z and y, as well as dependencies between components of z and components of y. To build a TT for continuous variables, the protocol can introduce a categorical random variable $s_k \in \{1, \ldots N_k\}$ for each component $z_k$. The joint distribution becomes:

$$p_\psi(z,y) = \Sigma_{s_1, \ldots, s_d} p_\psi(z,s,y) = \Sigma_{s_1, \ldots, s_d} p_\psi(s,y) p_\psi(z|y,s) \quad (7)$$

For conditional distribution $p_\psi(z|y,s)$ a fully factorized Gaussian is chosen that does not depend on y:

$$p_\psi(z|y,s) = p_\psi(z|s) = \Pi_{k=1}^d \mathcal{N}(z_k | \mu_{k,s_k}, \sigma_{k,s_k}^2) \quad (8)$$

While distribution $p_\psi(z|y,s)$ does not model dependence between z and y, the overall model still captures dependencies in $p_\psi(s,y)$ term. The distribution $p_\psi(s,y)$ is a over discrete variables and can be seen as a tensor $p_\psi(s,y) = W[s_1, \ldots, s_d, y_1, \ldots, y_n]$. The tensor W is stored in the Tensor Train or Tensor Ring format. The resulting distribution used as a prior model becomes:

$$p_\psi(z, y) = \sum_{s_1, \ldots, s_d} \underbrace{W[s_1, \ldots, s_d, y_1, \ldots, y_n]}_{p(s,y)} \underbrace{\prod_{k=1}^u \mathcal{N}(z_k | \mu_{k,s_k}, \sigma_{k,s_k}^2)}_{p(z|s,y)} \quad (9)$$

The VAE-TTLP can be defined with the learnable prior $p_\psi(z,y)$ parametrized by Tensor Train or Tensor Ring models. For example, $(x, y_{ob})$, where x is an object and $y_{ob}$ are observed values of conditions (e.g., properties). The evidence lower bound object (ELBO) for VAE with learnable prior is shown in Equation 3. For the VAE-TTLP model, it becomes:

$$\log p(x, y_{ob}) \geq \hat{\mathcal{L}}_{TTLP}(\theta, \phi, \psi) = \quad (10)$$
$$\mathbb{E}_{q_\phi(z|x,y_{ob})} \log p_\theta(x|z, y_{ob}) - \mathcal{KL}(q_\phi(z|x, y_{ob}) \| p_\psi(z|y_{ob})) + \log p_\psi(y_{ob})$$

The protocol makes two assumptions in order to apply the model to a subset conditioning problem. First, the protocol assumes that all information about values of y is contained in the object x itself. This is a reasonable assumption—for example, if want to generate a hand-written digit (x), information about its label (y) is already contained in x. Under this assumption, $q_\phi(z|x,y_{ob}) = q_\phi(z|x)$. The model also assumes $p_\theta(x|z,y_{ob}) = p_\theta(x|z)$. As such, the object is fully defined by its latent code. This results in a final ELBO:

$$\log p(x, y_{ob}) \geq \mathcal{L}_{TTLP}(\theta, \phi, \psi) = \quad (11)$$
$$\mathbb{E}_{q_\phi(z|x)} \log p_\theta(x|z) - \mathcal{KL}(q_\phi(z|x) \| p_\psi(z|y_{ob})) + \log p_\psi(y_{ob}) \approx \approx$$
$$\frac{1}{l}\sum_{i=1}^l \left[\log p_\theta(x|z_i) - \log \frac{q_\phi(z|x)}{p_\psi(z|y_{ob})}\right] + \log p_\psi(y_{ob}).$$

Wherein $z_i \sim q_{\phi(z|x)}$. Since the joint distribution $p_\psi(z,y)$ is parameterized in TT format, the model can compute posterior distribution on the latent code given observed conditions $p_\psi(z|y_{ob})$ analytically. The model can also fill in missing conditions by sampling $p_\psi(y_{un}|z)$.

The trained VAE-TTLP model can be used to produce conditional samples from $p(x|y_{ob})$. The protocol can sample from this distribution by first sampling the latent code $z \sim p_\psi(z|y_{ob})$ and then feeding it to the decoder $x \sim p_\theta(x|z)$. Sampling of z can be efficiently done using the chain rule: $p(z|y_{ob}) = p(z_1|y_{ob})p(z_2|y_{ob}, z_1) \ldots p(z_d|y_{ob}, z_1, \ldots, z_{d-1})$. The conditional distribution on $z_k$ is a Gaussian mixture with unchanged centers $\mu_{k,s_k}$ and variances $\sigma_{k,s_k}^2$, but with weights different from w:

$$p(z_k | y_{ob}, z_1, \ldots, z_{k-1}) = \frac{p(y_{ob}, z_1, \ldots, z_{k-1}, z_d)}{p(y_{ob}, z_1, \ldots, z_{k-1})} = \quad (12)$$
$$\frac{\sum_{s,y_{un}} W[s, y_{ob}, y_{un}] \prod_{i=1}^k \mathcal{N}(z_i | \mu_{i,s_i}, \sigma_{i,s_i}^2)}{\sum_{s',y_{un}} W[s', y_{ob}, y_{un}] \prod_{i=1}^{k-1} \mathcal{N}(z_i | \mu_{i,s_i'}, \sigma_{i,s_i'}^2)} =$$
$$\sum_{s,y_{un}} \left[\frac{W[s, y_{ob}, y_{un}]}{\sum_{s',y_{un}} W[s', y_{ob}, y_{un}]}\right] \mathcal{N}(z_k | \mu_{k,s_k}, \sigma_{i,s_k}^2)$$

Weights of components can be efficiency computed, since W is represented in Tensor Train or Tensor Ring format. The overall architecture is schematically shown in FIG. 1. FIG. 1 shows a schematic representation of the VAE-TTLP model 100. The Autoencoder is trained to map object x to the latent code z. Joint distribution on conditions (e.g., properties) y and the latent code z is trained in Tensor-Train format. This model can be used to generate samples from a subset of all possible conditions. For example, the protocol can condition samples on properties $y_1$ and $y_3$ without specifying $y_2$. That is, $y_2$ is unknown or not used. As shown, the image 102 is provided to the encoder 104, where the data for the image 102 is processed in view of the conditions $y_1$ and $y_3$, but where condition $y_2$ is unknown. The image 102 can be a series of images 102, which are used to train the model 100 as described herein. The latent space 106 results in the latent codes $z_1$, $z_2$, $z_3$, $z_4$, and $z_5$, etc. based on the conditions $y_1$ and $y_3$. The latent codes are then processed through the decoder 108, which then reconstructs the image 102 to provide the reconstructed image 110.

As shown, the $y_2$ unknown, but the protocol can still work because of the Tensor Train decomposition. The object can be correlated with properties, such as properties of features that are visible in the object. When the object is an image of a person, the hair length, hair color, gender, with or without glasses can be the properties. In a molecule, the different functional groups and three-dimensional orientation of the structure may be properties, but also the physiochemical properties, such as biological activity, melting point, solubility, and others may be the properties. As such, with molecules, some properties may be unknown. However, the Tensor Train may operate so that the VAE-TTLP model can still produce molecules with desirable properties independent of whether or not the desired properties have values that are known (e.g., whether or not solubility is known, where the generated molecule has the desired solubility). The object that is produced can include features that are defined, whether present or absent from the features in the dataset.

The encoder produces the distribution on the latent code, then we obtain sample z from latent distribution, which is a multi-component vector. The vector is processed through the decoder to reconstruct the object. FIG. 1 show a vector with 5 components, $z_1$-$z_5$. However, any number of components can be used. The model can be trained so that the object x that is processed in the encoder 104 is the same as the reconstructed object $\tilde{x}$ from the decoder 108. The distribution of the latent code z can be shaped so that latent code z contains some information about y or the properties. The model can parameterize the joint distribution of z and y in the Tensor Train format, to allow for sample latent codes given by information of the properties. As shown, this is why $y_2$ may be unknown or undefined. The latent code is then sampled from the distribution of latent codes, and the sampled latent code is passed through the decoder 108 in order to generate the reconstructed image $\tilde{x}$.

In some embodiments, the latent code from the encoder that has been trained by be enhanced for procuring objects with the desired conditions. The use of the Tensor Train and the computation of the probability of samples under the given object along with the KL divergence improve the generation of a proper object with the desired conditions.

The following information provides technical details for training the VAE-TTLP model. First, mixture weights $w[s_1, \ldots, s_d, y_1, \ldots, y_n]$ should be non-negative and sum up to one. To ensure non-negativity, the protocol replaces negative components of core tensors $Q_k$ with their absolute values. The protocol also stores a non-normalized tensor computing normalization constant on the fly in polynomial time.

A well-known problem with Gaussian mixture model is collapsing of mixture components. During the training, it may be observed that weights of many components quickly degraded to zero, resulting in a less expressive prior distribution. It is hypothesized that this may occur due to the poor optimization procedure. To prevent component collapse, the protocol reinitializes mixture parameters $\mu_{k,s_k}$ and $\sigma_{k,s_k}^2$ several times during the training process using a two-step procedure. First, the protocol samples latent codes from the distribution $z \sim q_\phi(z|x)$ and for each latent space dimension k the protocol estimates parameters mean $\mu_{k,s_k}$ and variance $\sigma_{k,s_k}^2$ of a Gaussian mixture $p_\psi(z_k) = \Sigma_{s_k} \pi_{s_k} \mathcal{N}(\mu_{k,s_k}, \sigma_{k,s_k}^2)$ using the Expectation-Maximization algorithm. For the second step, the protocol fixes means and variances of the prior $p_\psi(z,y)$ and optimize cores of the Tensor Train represented $W[s_1, \ldots, s_d, y_1, \ldots, y_n]$. As a result, an obtained prior distribution (e.g., learnable prior) uses mixture components more efficiently, increasing the performance of the overall model.

Modern deep generative models are usually separated into two main categories. The first category is related to Generative Adversarial Networks (GAN), and the second one corresponds to models similar to Variational Autoencoders (VAE). Generative Adversarial Network is a model consisting of two networks—a generator and a discriminator. The generator produces a set of novel objects, while the discriminator tries to distinguish them from real ones. Variational and Adversarial Autoencoders build an autoencoder model with a regularizer that shapes the latent space. GANs produce state-of-the-art samples in specific domains, but Autoencoder-based approach allows training with discrete data and prevents the mode collapse problem.

Figure 5:
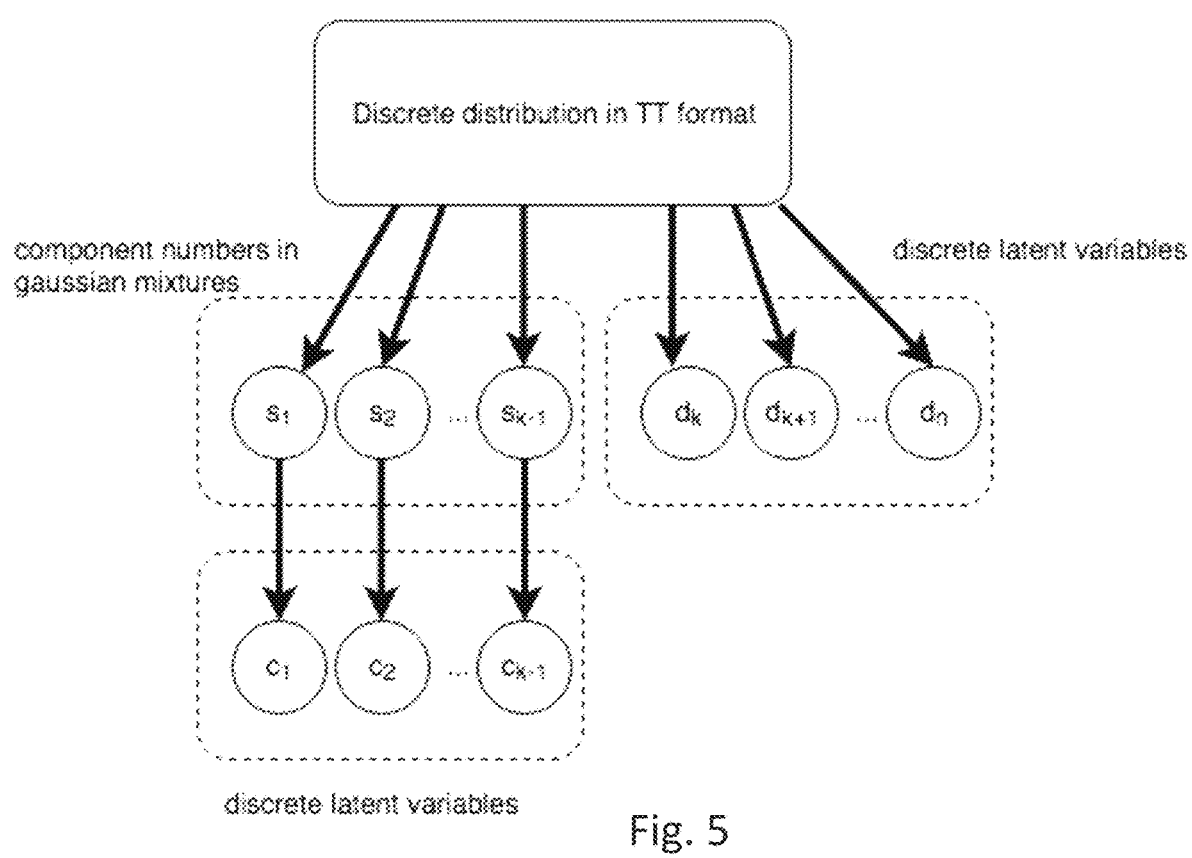
FIG. 5 includes a schematic representation of the distribution of continuous and discrete latent variables modeled by Tensor Train decomposition approach.

In some embodiments, the VAE-TTLP model can combine an autoencoder with a learnable prior that is parametrized by Tensor Train or Ring Tensor (also referred to as a Tensor Ring) decomposition. The Tensor Train (TT) decomposition is used to represent large high-dimensional tensors with a restricted number of parameters. Thus, TT decomposition is especially useful to store high-dimensional discrete distributions. To make the TT capable of handling continuous random variables the distribution on each continuous variable is modeled by a mixture of Gaussians. Then, the TT decomposition will store a discrete distribution of discrete latent variables and discrete numbers of components which models continuous variables. The concept is illustrated on the FIG. 5. As shown, the discrete distribution in the TT format goes to the: (1) component numbers in Gaussian mixtures shown by "s"; and discrete latent variables shown by "d". The component numbers in Gaussian mixtures then goes to the discrete latent variables shown in "c". Accordingly, when the condition is not known, the component numbers in Gaussian mixtures can be used to determine discrete latent variables "c" TT decomposition is widely applied in machine learning to efficiently represent tensors with a small number of parameters. TT decomposition is also sometimes used to compress fully-connected, convolutional or recurrent layers of neural networks. In the VAE-TTLP model, the TT decomposition for discrete distributions is used to allow computing marginal and conditional distributions.

Unlike other models with a learnable prior, the VAE-TTLP model learns dependencies not only between latent variables, but it also learns: (a) cross dependencies between object properties and latent space; and allows (b) arithmetically efficient marginalizing (e.g., integration over some set of variables) and conditioning (e.g., modifying the learnable prior to have more density on objects that has properties the model was conditioned on). Both properties (a) and (b) allows the sampling of latent variables to produce objects with predefined properties.

In some embodiments, the architecture of the VAE-TTLP model uses an 8-layer neural network convolutional neural network with 6 convolutional and 2 fully connected layers for the encoder and a symmetric architecture with deconvolutions for the decoder.

In some embodiments, the training procedure used by the VAE-TTLP model architecture is similar to the training for a usual VAE architecture. Nevertheless, there are some differences due to the presence of the learnable prior, which handles both latent variables and object features (that can have some missing variables). In some aspects, the training can be performed with a stochastic gradient descent using an Adam optimiser with a learning rate equal to 0.0001.

Figure 3A:
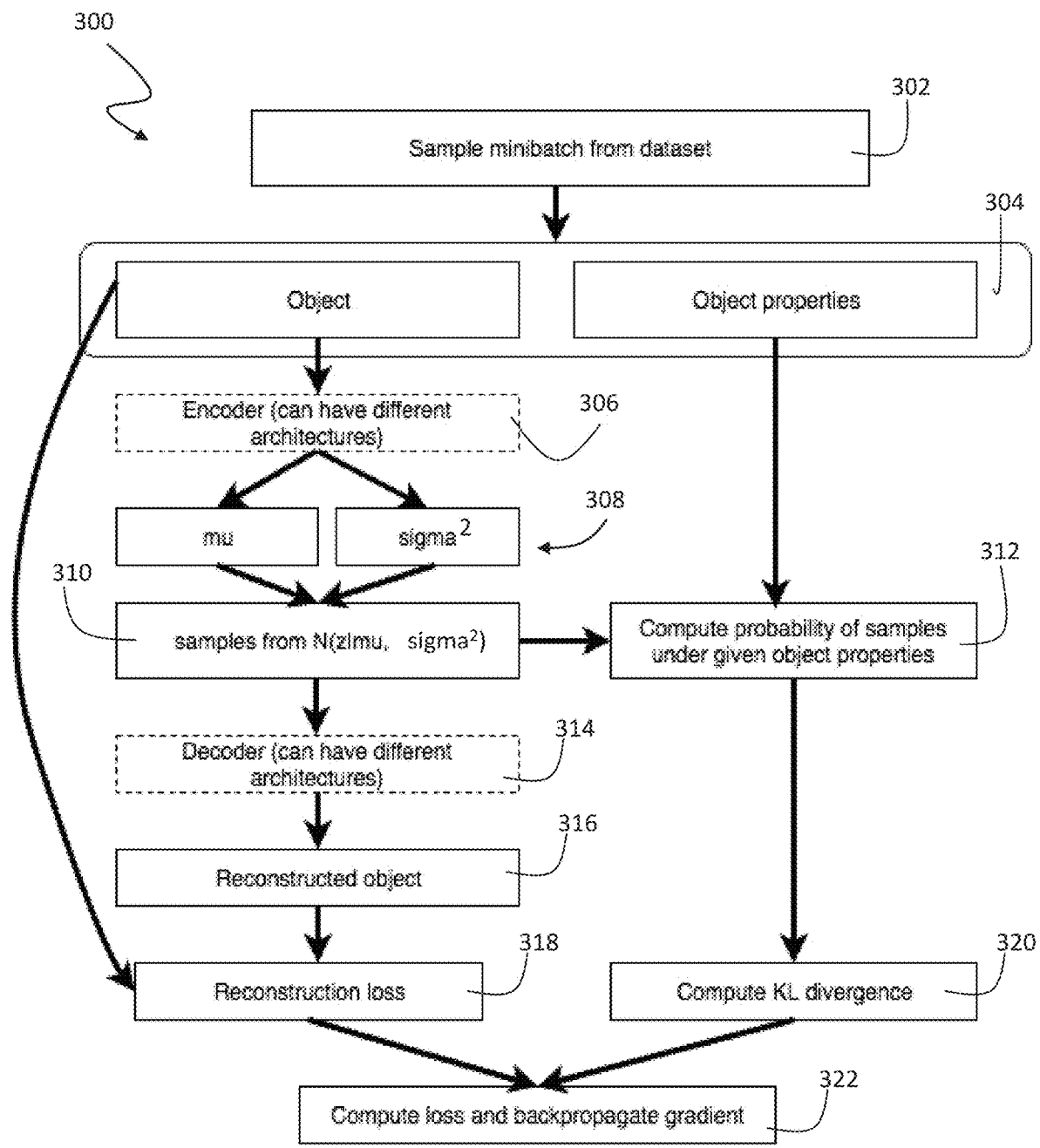
FIG. 3A includes a flowchart for a protocol for using the VAE-TTLP model.

For each iteration of stochastic gradient descent (SGD), the following steps are performed, which are shown in FIG. 3A. Note that sub-steps d, e, and f deviate from standard VAE training. Step 1—Sample minibatch of objects $\{x1, \ldots, x_n\}$ and their properties $\{y_1, \ldots, y_n\}$. Step 2—For each object with index i from the minibatch, do the following sub-steps: a) Run encoder on objects and obtain latent variables distributions $N(z_i|x_i)$; b) Sample a latent variable from obtained distribution $z_i \sim N(z_i|x_i)$; c) Run decoder and obtain logarithm of probability $\log p(x_i|z_i)$ for the sampled latent variable from obtained distribution (in a case of images, it's just a mean squared error of generated object and original one over all pixel and all color channels); d) Compute entropy of $N(z_i|x_i)$; e) Compute logarithm of prior probability $\log p(z_i|y_i)$; f) Subtract the obtained log probability from the entropy to obtain a one-point approximation of KL divergence; and g) Reduce value obtained on sub-step (c) from value on sub-step (f), obtain ELBO (evidence lower bound object) estimation. Step 3—Compute the mean of all ELBOs obtained on sub-step (g) on whole minibatch. Step 4—Perform the gradient descent step.

As shown in the method 300 of FIG. 3A, the sample minibatch is obtained from a dataset (302). The object and object properties are then considered (304). The object is processed through the encoder (306) and mu ($\mu_{k,s_k}$) and sigma$^2$ ($\sigma_{k,s_k}^2$) are obtained (308). Samples from the distribution of $z_i(\mu_{k,s_k}, \sigma_{k,s_k}^2)$ are then obtained (310) and used with the object properties to compute the probability of samples being obtained under the given object properties (312). The samples latent codes are then processed through the decoder (314), and the reconstructed object is obtained (316). The reconstruction loss is then calculated for the reconstructed object (318). The KL divergence is calculated (320). The loss is calculated and the gradient is back-propagated (322).

The following steps can be used for generating a reconstructed object as well as training the model to be capable of generating such a reconstructed object. Step 1 can be to provide the object data to the encoder. Step 2 can be to sample the latent code. Step 3 can be determining the joint probability of samples of the latent code having the property (specified conditions), such as desired property or defined property. The model can be trained to maximize this probability obtained from Step 3. As such, the model optimizes the latent code in view of the properties. This can be seen in FIG. 3A.

The protocol can start with sampling the dataset, which can be by randomly select a few objects from the data set. For example, the dataset can include the objects and the object properties. For image objects, the properties can be features. For molecule objects, the properties can be biological activity, structure properties, and physical properties.

The object data is processed by the encoder (306) to produce mu ($\mu$—mean of distribution) and sigma$^2$ ($\sigma$—variance), which define the distribution of the latent code z. As such, the latent code z can have a distribution of vectors. It should be noted that the variance is sigma squared ($\sigma^2$—variance). This indicates where the object is placed in the latent space.

Then sample from the distribution to get the latent code z (310), which can be a normal distribution, and then pass it through the decoder (314) to get the reconstructed object 316. After obtaining the reconstructed object 316, the reconstruction loss is calculated based on the original object and the reconstructed object, where information that is lost from the original object can be determined (318, FIG. 3A). This determines the dissimilarity be the original object and the reconstructed object. The goal from training the model is for the dissimilarity to be zero.

Also, element 312 shows the samples of the distribution of the latent code is used with the object properties to compute the probability of the samples being under given object properties. To compute the probability under the samples under the given object properties, the tensor train decomposition is used to compute the probability that the samples comply with the object properties. To determine whether the object from the samples from the $\mu$ (mu) and $\sigma^2$ (sigma squared), the model processes it with the Tensor Train Decomposition. As such, latent code z can be compared to distribution of conditions/properties for the objects, then determine the probability of z to have the desired properties. If the properties distribution for latent code matches the distribution of latent codes from the encoder, the model is operating, but if not, then the model may be further trained or the parameters may be modified for the desired properties so that the distribution of latent codes matches the distribution of latent codes having the property.

Then, under element 320, the model can compute the KL divergence to determine how the joint probability behaves. In the ideal case this loss would be 0, and less ideal is when the latent code does not match the object properties so that will result in some number other than 0. The KL divergence can be computed by Equation 11. The KL divergence measures the different distributions from the encoder and Tensor Train.

Then, the loss is computed from the reconstruction loss and KL divergence, with the back propagated gradient (322).

Figure 3B:
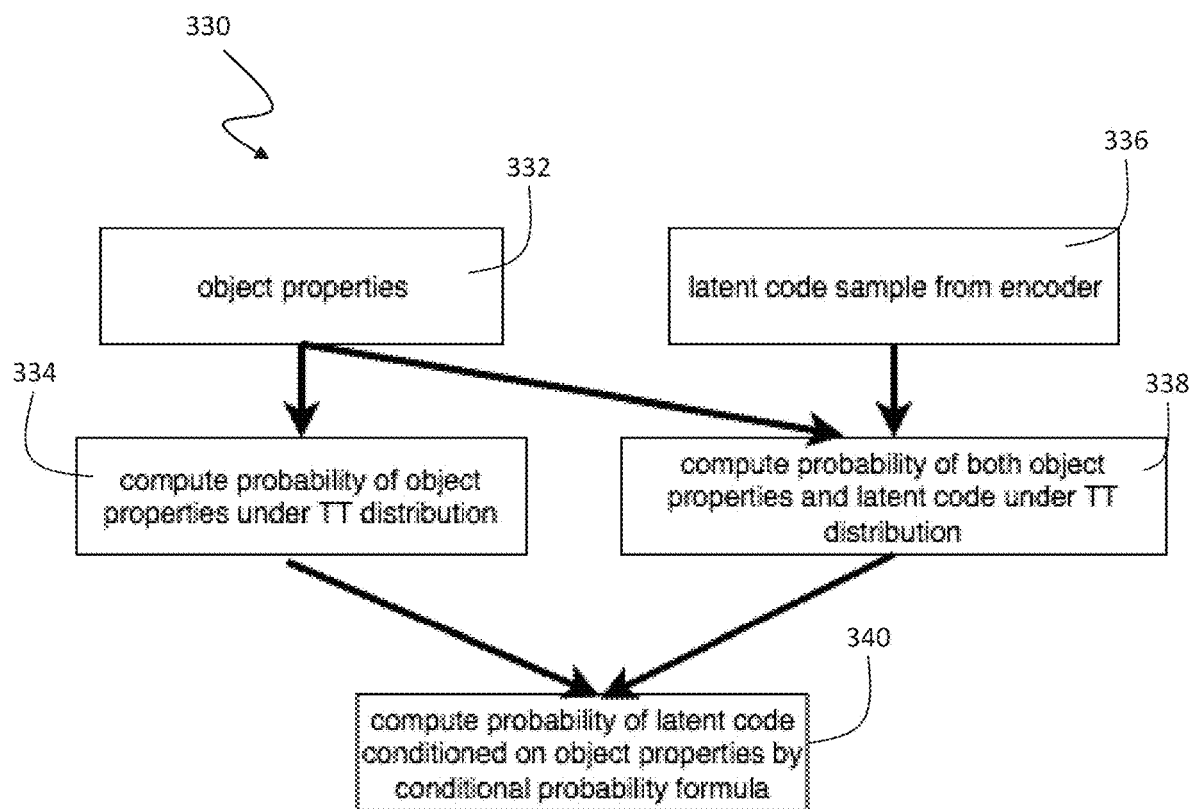
FIG. 3B includes a flowchart describing the steps for computing the probability of samples under given object properties.

FIG. 3B includes a flowchart describing the steps for computing the probability of samples under given object properties. FIG. 3B can be the method of element 312 of FIG. 3A for computing the joint probability of samples under the given object properties. Accordingly, FIG. 3B shows a method 330 where the object properties are provided (332) and used for computing the probability of object properties under a TT distribution (334). Also, the latent code sample from the encoder is obtained (336) and used with the object properties to compute the probability of both object properties and latent code under the TT distribution (338). The computed probability of 334 and of 338 are then used to compute the probability of a latent code conditioned on object properties by a conditional probability formula (340).

For example, obtain examples from the minibatch dataset, and samples from the latent code. Then Equation 9 is used to calculate the probability (e.g., 312). The conditional probably of the latent code z given the property y is determined.

Figure 3C:
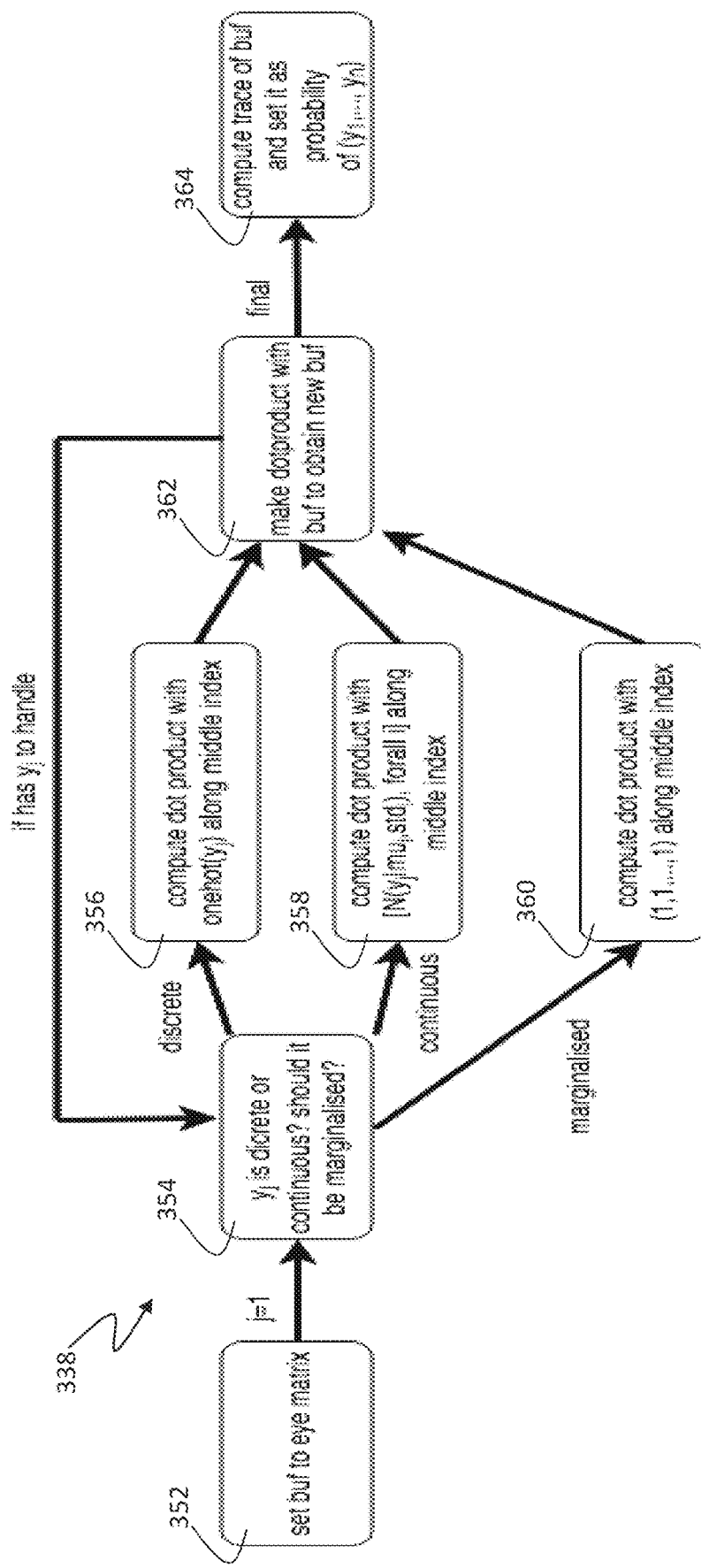
FIG. 3C includes a flowchart describing the detailed steps for computing the probabilities of object properties.

FIG. 3C includes a flowchart describing the detailed steps of a method 350 for computing the probabilities of object properties. As such, FIG. 3C shows the protocol for performing the computations of probability of FIG. 3B, such as in element 338. The method 338 includes setting the buffer (buf—an intermediate vector stored in memory) to eye matrix, with j=1 (352). Then, it is determined whether or not the $y_j$ is discrete or continuous, and whether or not it should be marginalized (354). If discrete, the discrete pathway is followed, which includes computing the dot product with onehot($y_j$—a vector that contains 0s everywhere except position of $y_j$, and the position of $y_j$ contains 1) along the middle index (356). If continuous, compute the dot product with [N($y_j$|mu$_i$, std$_i$), for all i] along the middle index (358). If marginalized, compute the dot product with (1, 1, ..., 1) along the middle index (360). Then, the result if discrete, continuous, or marginalized is then processed to make the respective dot product with the buffer (buf) to obtain a new buffer (buf) (362). Then, the process computes the trace of the buffer (buf) and set it as the probability of ($y_1, \ldots, y_n$) (364). However, before computing the trace of the buffer (buf), if there is a $y_j$ to handle, the process iterates back to step 354 and the determinations are made, and the process is repeated as shown.

Also, FIG. 3C shows the protocol for discrete and continuous conditions or properties. However, when the property is not defined or specified, then the marginalized protocol can be performed.

Figure 6:
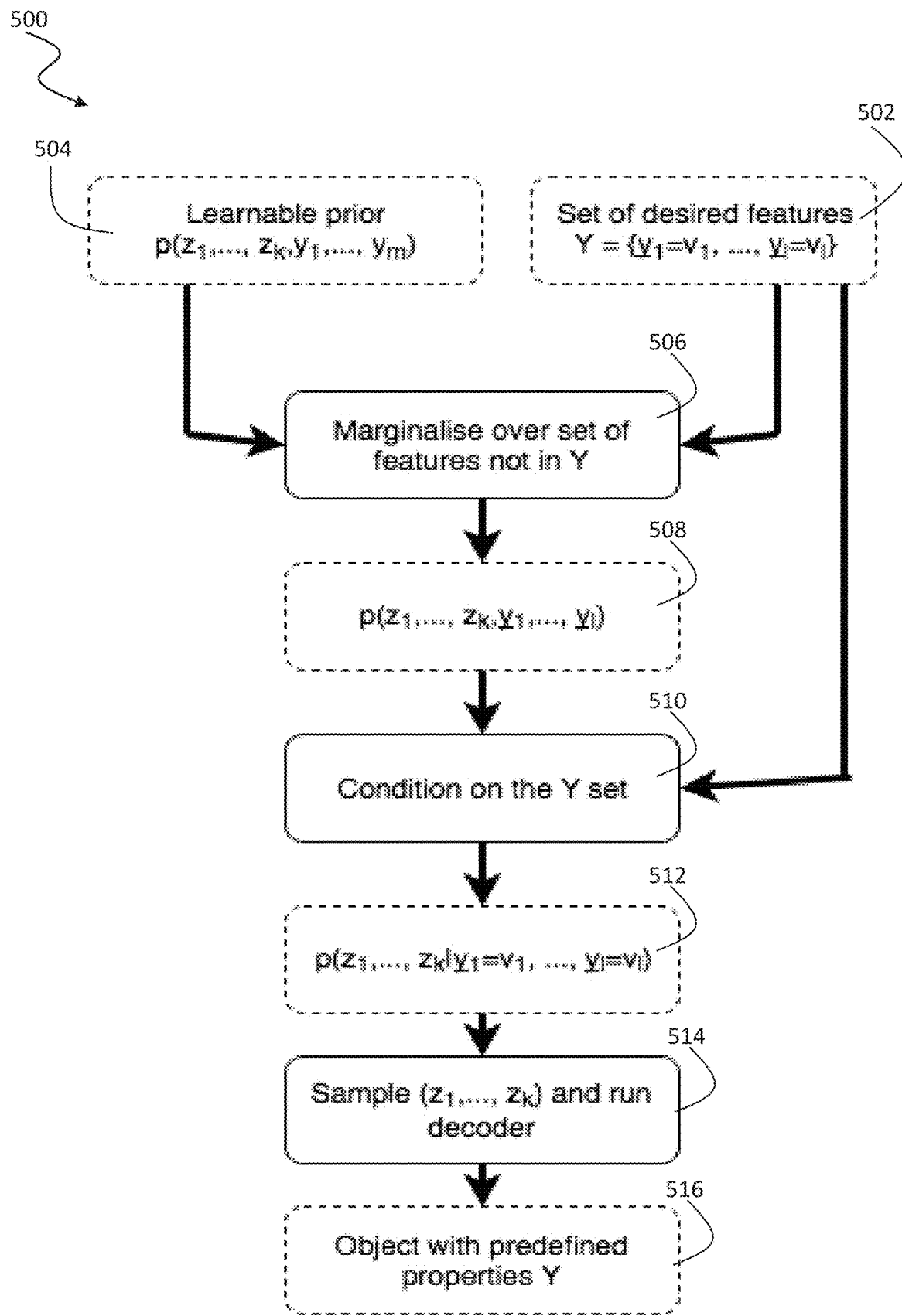
FIG. 6 includes a flow chart describing the details of generating an object with desired properties using the VAE-TTLP model.

In some embodiments, the results from the element 312 can be used to train the model so that the encoder produces better latent codes that can be used to generate better reconstructed objects with the desired properties. In FIG. 6, the joint model samples the latent codes z given some y, and the method produces the reconstructed object having the desired properties. The properties can already be embedded in the objects, and the objects are selected with those properties. In some instances, the reconstructed object is used to calculate the reconstruction loss, on the other side, the KL divergence is calculated.

FIG. 4 show a method 400 for the generation of objects with desired properties using the VAE-TTLP model. As shown, the desired object properties are defined (402). A sample latent code is then obtained from the TT distribution that is conditioned with the desired object properties (404). The decoder then generates the reconstructed object, which has the desired object properties (406).

In view of the foregoing, the computing probability in the Tensor Train (TT) with the learnable prior is described. The procedure to compute the probability in TT with a learnable prior is schematized on the FIG. 2 with a tensorial computation graph. The nodes of this graph are tensor, whereas the edges between nodes represent tensor contraction operation. Since contraction is a commutative operation, contraction can be done following any order. Tensors {Qi} are the core objects of the TT decomposition. They are contracted with values of random variables. The discrete variables are represented by one-hot vectors, which can be handled as 1-dimensional tensors. The continuous variables are modeled by a mixture of normal distributions and consequently it is described as vector of probabilities inside a components of mixture. If the value of some variable is missing, it is represented as a vector filled with ones. After performing all contractions there is only one non-negative value which is equal to the probability of the vector of variables inside the TT distribution.

Figure 2:
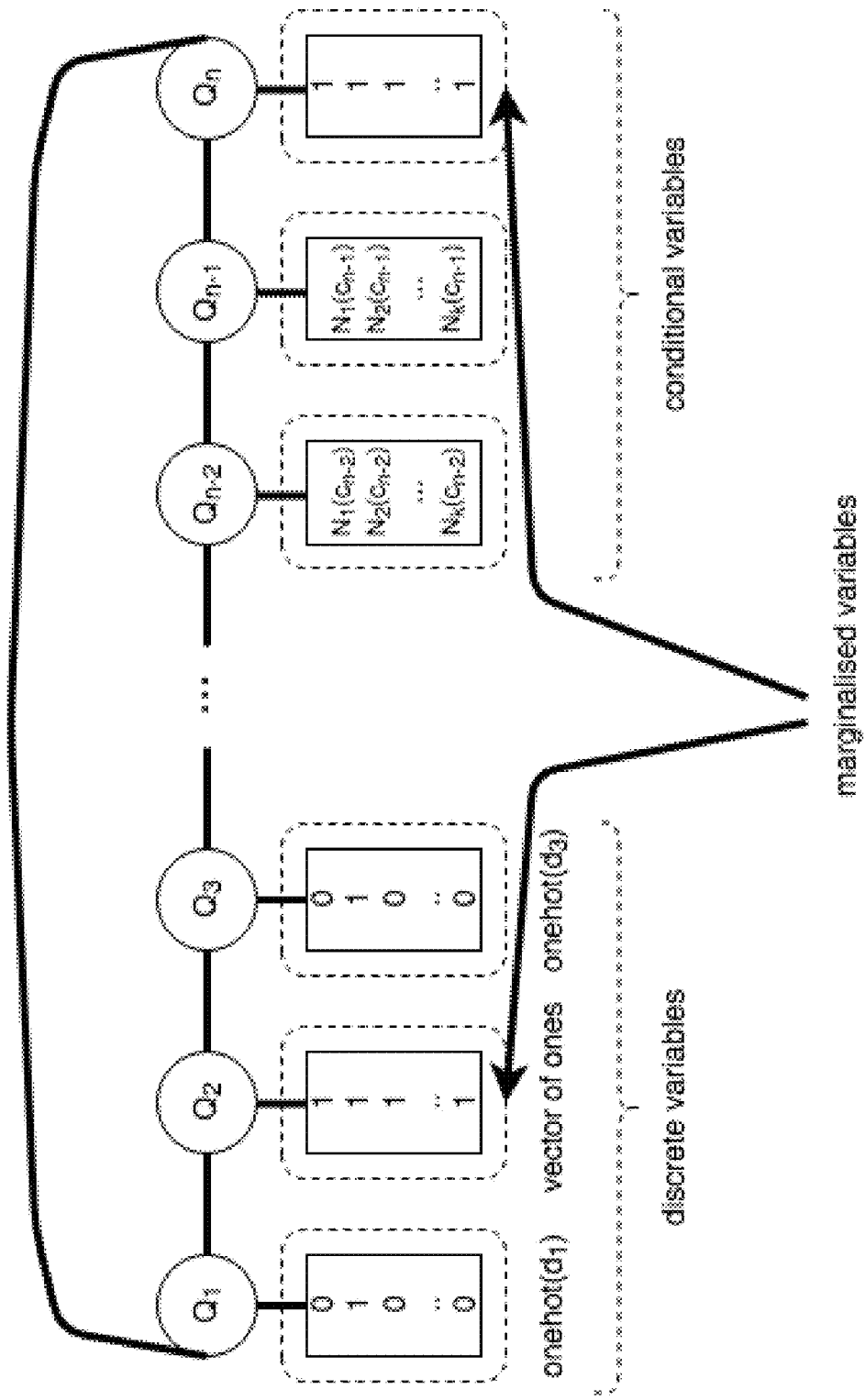
FIG. 2 includes a schematic representation for computing the probability of the latent variable set under Tensor Train modeled distribution.

FIG. 2 can be considered a more detailed description of FIG. 3C. There are discrete variables and continuous variables. There may be a multi-dimensional tensor, such as for example, vector is a one dimensional tensor, matrix is a two dimensional vector, and with more dimensions it can be referred to as a tensor. A joint distribution can be obtained as described. For example, for discrete random variables then specify the joint distribution at the tensor. If having two variables, such as R1 and R2, the probability of R1 equals R2 could be written in a two dimensional tensor. As such, the variable can be represented in the Tensor Train format used for Tensor Train decomposition. The methodology allows for exploring tensors that have a large number of tensors that may not be able to be stored in memory.

The VAE-TTLP model can be used to generate objects with pre-defined properties, when the objects used to train the model may have some missing properties. As such, the model can operate even with only some known properties and other properties of the objects being unknown.

FIG. 6 shows a method 500 for generating objects with pre-defined properties under the principles described herein. First the desired properties to be obtained from the generated object must be formulated (502). The desired properties can be a subset of all properties used for training. The learnable prior of the model (504) is used in the method 500 to marginalize the learnable prior over properties that are not included the desired properties set (506) to obtain the $p(z_1, \ldots z_k, y_1, \ldots y_j)$ (508). The next step is to make the conditioning of marginalized learnable prior over properties in the set (510). This step (510) provides the distribution over latent space $p(z_1, \ldots, z_k | y_1 = v_1, \ldots, y_j = v_j)$ (512), which have high density in areas producing object with given properties. Finally, the latent variable is sampled from the conditioned prior (514) to obtain the object with the pre-defined properties by running the decoder on this sampled latent vector (516).

Figure 4A:
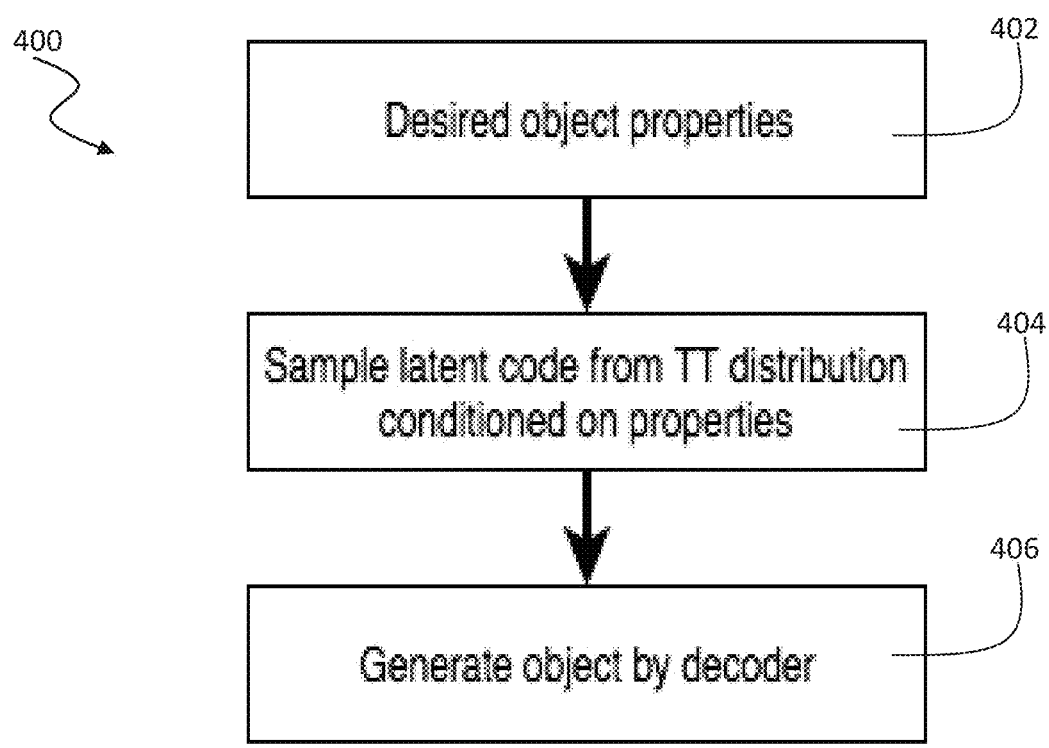
FIG. 4A includes a flowchart describing the generation of objects with desired properties using the VAE-TTLP model.

Accordingly, FIG. 6 is a more detailed description of the subject matter of FIG. 4A, where how to sample the latent code and obtain the resulting object. The learnable prior is obtained from the general distribution of z and y. The set of desired features contains few values we want object to have, not presented features can take any value for generated object. The method 500 marginalizes the learnable prior in view of features that not present. There is the probability of the latent code that is specified with the y. Then use it to compute the conditional probability over the latent code given the specified values of y. Then, sample from the distribution of the latent code z and then process it through the decoder to get the reconstituted object.

While the VAE-TTLP model has been described with regard to objects, which can be images, the model may also be used to generate chemical structures that have desired properties. As such, the properties of the molecular objects may have some missings, and the VAE-TTLP can be used to generate molecular objects that have the desired properties even though some properties of the objects are not available.

Extended Models

The VAE-TTLP model has been described herein. Now, the VAE-TTLP model can be used with Reinforced Learning (RL). The RL protocols can be used to introduce rewards for generation of novel objects, such as novel molecular structures. While the RL protocols can be described in connection with molecular structures, they can also apply to the other types of objects, such as images, video, audio, text, and other objects.

The VAE-TTLP model can also be used in a combination with Reinforcement Learning (RL) framework to expand the structure of the latent manifold (e.g., latent space) towards novel chemical structures, such as novel inhibitors of protein or other biological activity. The RL protocol can use the REINFORCE algorithm for training, which directly optimizes the policy using the log-derivative scheme. The protocol can include fixing all parameters of the encoder and decoder (except first fully connected layer), and only training the complex distribution of the manifold $p_\psi(z)$ (a learnable prior) in the latent space and first layer of decoder. The protocol can expand the latent space with exploration batches containing molecules reconstructed from outside the current manifold (e.g., latent space 106 FIG. 1). The protocol can include estimating the mean $\mu$ and the variance $\sigma^2$ of $p(z)$ for all dimensions, and then sample exploration codes from $z^{exploration} \sim U(\mu-2\sigma, \mu+2\sigma)$. The protocol can pass these codes through the decoder $x^{exploration} \sim p_\theta(x|z^{exploration})$ and evaluate the reward for obtained molecules $\{x^{exploration}\}$. If the reward for a newly explored area is high, the latent manifold will expand towards it. The manifold is formed by a shape in multi-dimensional space from the latent space of the different objects.

The RL can be implemented with a VAE-TTLP model that is at least partially trained, and the RL may further train the model for improved generation of the reconstructed object. This may be helpful when using the VAE-TTLP in the space of chemical structures because certain features may be reinforced with rewards to improve the design of a molecule with particular properties. The latent codes can be randomly sampled near some known nodes of a chemical structure so that the variable features can be analyzed. For example, a certain loci in a molecule can be derivatized with various substituents.

In some embodiments, the protocol helps shape the output from the manifold, which can be the latent space with the conditions as shown by element 106 in FIG. 1.

The protocol can sample $z^{exploration}$ which can be from a structure outside of the manifold. As such, the sample can be from the $z^{exploration}$ as latent codes, and then the probability can be determined for the probability that these samples under the given object properties. These sampled $z^{exploration}$ latent codes can then be processed through the decoder to generate an exploration reconstructed object. Then the loss can be computed to determine how well the exploration reconstructed object matches the original object. There can be a reward for the $z^{exploration}$ latent code. If the reward is high, then the latent manifold expands toward the $z^{exploration}$ latent code. If not, then the latent manifold expands away from it, or expands toward a different $z^{exploration}$ latent code that has a higher reward.

Reward Function

A reward function was developed on the basis of Self-Organizing Kohonen Maps (SOMs). This algorithm was introduced by Teuvo Kohonen as a unique unsupervised machine-learning dimensionality reduction technique. It can effectively reproduce an intrinsic topology and patterns hidden into the input chemical space in a consistent and unbiased fashion. The input chemical space is usually described in terms of molecular descriptors (input vector), while, at the output a 2D- or 3D-feature map convenient for visual inspection is generated. An ensemble of three SOMs was used as a reward function: the first SOM was trained to predict the activity of compounds against kinases (General Kinase SOM), the second one was developed to select compounds located in neurons associated with DDR1 inhibitors within the whole kinase map (Specific Kinase SOM), and the last one was trained to assess the novelty of chemical structures in terms of the current trends in medicinal chemistry (Trend SOM). During learning, the basic AI-model was rewarded when the generated structures were classified as molecules acting on kinases, positioned in neurons attributed to DDR1 inhibitors as well as tended to be relatively novel structures.

General Kinase SOM

The pre-processed training dataset included of total 41K small-molecule compounds: 24K kinase inhibitors and 17K molecules with the reported activity (at the concentration of <1 µM) against non-kinase targets. For the whole database more than 2K molecular descriptors were calculated using RDKit, Mordred library, and SmartMining Software. Descriptors were ranked in accordance with bivariate Student's t-values and then 9 descriptors were selected as the most privileged and theoretically valid for distinguishing between kinase and non-kinase chemistry. The set included: MW (molecular weight, t=−63.4), Q' (binormalized quadratic index, t=77.3), SS (common electrotopological index, t=−69.3), S[>C<] (partial SS index, t=−50.3), 1 Ka (1st Kier topological index, t=−66.5), Hy (hydrophilicity index, t=−55.9), VDWwvol (weighted atomic Van der Waals volumes, t=−70), HBA (number of hydrogen bond acceptors, t=−34.0), HBD (number of hydrogen bond donors, t=−8.5), and RGyr (Radius of gyration, t=−55). The map size was 15×15 2D-representation (random distribution threshold was 177 molecules per neuron), learning epochs: 2000, initial learning rate: 0.3 (linear decay), initial learning radius: 8, winning neuron was determined using Euclidean metrics, initial weight coefficients: random distribution. After the training process was completed, the areas populated by kinase inhibitors and molecules acting on other biological targets were highlighted. We observed that compounds from these two categories were mainly located in distinct regions within the common map. Neurons were then prioritized based on the following privileged factor (PF): NiK(%)/NiNK(%), where NiK is the percent of kinase inhibitors located in i-th neuron, while NiNK is the percent of other molecules located in the same neuron and vice versa. PF value greater than 1.3 was used as a threshold to assign neurons to one of these two classes. There were no "death" neurons within the map. Average classification accuracy was 84% with a random threshold. All the generated structures were scored using this model during learning cycles as well as at the prioritization step. Compounds which were classified as kinase inhibitors with the lowest error (Euclidean metrics) were subsequently subjected to the specific kinase SOM.

The general kinase SOM can trend to molecule or loci in molecules that are involved in interacting with a kinase.

Specific Kinase SOM

A similar procedure was performed to construct a Kohonen map for the identification of elements assigned to DDR1 inhibitors along the kinase inhibitors chemical space. Structures which were classified as kinase inhibitors by the general kinase SOM were used as an input chemical pool. The final set of molecular descriptors included: MW (t=−44), Q' (t=37), 1 Ka (t=−42), SS (t=−52), Hy (t=−30), VDWsumvol (t=−35), HBA (t=−40), and HBD (t=14). Map size was 10×10 2D-representation (random distribution threshold was 245 molecules per neuron), the learning settings were identical to that applied for the general kinase SOM, except the initial learning radius which was equal to six. After the map was constructed, we identified neurons containing at least one DDR1 inhibitor. The formal average classification accuracy was 68% and the bias towards DDR1 inhibitors was observed. "Active" neurons were then used to select structures during the learning procedure to reward the core GENTRL and for the prioritization process. This case, we did not use PF for the selection decision to overcome over-training and to enhance novelty for the generated structures operating around close topographic proximity.

The specific kinase SOM can be similar to the general kinase SOM; however, the specific kinase SOM trends to chemistry for a specific type of kinase. That is, trends toward loci or functional groups known to interact with the specific kinase. For example, this may be used to design a novel inhibitor of DDR1. The reward can cause the reconstructed objects to have chemical features, such as chemical moieties, functional groups, or loci that are known to interact with DDR1.

Trend SOM

As an additional reward function, the protocol can also use the Kohonen map, which was developed based on the training dataset of molecules. The following key molecular descriptors were selected for training procedure: MW, Log P (lipophilicity, the calculated partition coefficient in octanol-1/water system), Log Sw (solubility in water), PSA (polar surface area, Å2), HBA, Don, SS, BFL (Beyond-Flatland Function). The BFL function correlates well with the chemical evolution and reflects true non-planarity of molecules versus simple sp3-rate. BFL is a sufficiently sensitive to follow the tendencies observed in modern medicinal chemistry in terms of novelty. The map size was 15×15 2D-representation (random distribution threshold was 75 molecules per neuron), learning epochs: 2000, initial learning rate: 0.4 (linear decay), initial learning radius: 10, winning neuron was determined using Euclidean metrics, initial weight coefficients: random distribution. After the training process was completed, the areas containing compounds claimed in different time periods were displayed and molecules which have been described in relatively new patent records (claimed between 2015-2018) ended up in a separate region of the map, whereas "old" chemistry is positioned predominantly in a radically distinct area providing a statistically relevant separation. Within the map, we have clearly observed an intrinsic trend through the years and depict it as a set of simple vectors. Neurons attributed to novel chemistry (the last decade) were used to reward our AI-core in contrast to neurons associated with "old" chemotypes.

In some instances, the trend SOM tries to predict the year the molecule was invented. It can be predicted that the molecule was determined to be in a certain year, which if recent can be novel chemistry, but if old then old chemistry. The reward function can tip toward recent chemistry in some instances so that relatively new molecules are explored.

Training Procedure

A training procedure can be used to train a VAE-TTLP model with reinforcement learning (Trend SOM, General Kinase SOM and Specific Kinase SOM). The following training procedure can be performed. Step 1—Obtain a trained VAE-TTLP conditional generative model. Step 2—Discard the encoder, and fix weights of all layers of the decoder except the first one (e.g., first layer weight not fixed). This allows for training the latent space and first layer of decoder. Step 3—Estimate mean $\mu$ and variance $\sigma$ for each dimension of the Tensor-Train induced prior $p_\psi(z)$. This can estimate the shape of the manifold. Step 4—Sample $z^{exploration} \sim U(\mu-2\sigma, \mu+2\sigma)$ for each dimension. Step 5—Pass $z^{exploration}$ through the decoder and obtain SMILES $x^{exploration}$ (e.g., simplified molecular input line entry system, or other). Step 6—Compute one or more rewards: $r_{trend}$, $r_{(general\ kinase\ SOM)}$, $r_{(specific\ kinase\ som)}$ for $x^{exploration}$. Step 7—Apply a single gradient ascent step to maximize total reward $r=validity*(r_{trend}+r_{general\ kinase\ SOM}+r_{specific\ kinase\ SOM})$ with respect to parameters $\psi$ of the Tensor-Train induced learnable prior $p_\psi(z)$ and the first layer of the decoder. Step 8—Repeat steps 3 through 7 until converged. For example, stop training when the reward stops increasing.

The molecules can be sampled, and then filtered by the pipeline protocols described herein. Then the molecules obtained by filtering can be synthesized and validated.

In some embodiments, the training procedure can be used to further train a trained VAE-TTLP model to provide the RL.

In some embodiments, all three SOMs may be used for training.

General Description

In some embodiments, a method for training a model to generate an object is provided. The method can include the following steps. The method can use a model configured as a variational autoencoder with a learnable prior, which is parameterized with a tensor train. Also, the method can use a dataset having object data for an object and condition data for a condition, wherein the condition may be a property of the object. The model can be used for processing the object data of the dataset to obtain latent object data with an object encoder of the model, wherein the latent object data includes a distribution of latent variables having a mean and a variance. The method can include sampling one or more latent variables from the obtained distribution of latent variables. The method can include processing the sampled one or more latent variables with defined object properties to compute a probability of the samples having the defined object properties. The method can include processing the samples one or more latent variables through an object decoder to obtain a reconstructed object. The method can include determining a reconstruction loss of the reconstructed object from an original object from the object data. The method can include computing a Kullback-Leibler divergence from the probability of the samples having the defined object properties. The method can include using the determined reconstruction loss and computed Kullback-Leibler divergence to compute a loss from the data set. The method can include performing a gradient descent until the reconstructed object is sufficiently representative of the original object and has the defined object properties. The method can include obtaining a trained model configured as a trained variational autoencoder with a learnable prior that is parameterized with a tensor train. Once obtained, the trained model can be provided for storage (e.g., computer memory) or use in generating reconstructed objects that have a desired property.

The method can be used for processing a plurality of objects in the dataset, such as the following: process object data with the object encoder to obtain latent variable distributions; sample one or more latent variables from the obtained latent variable distributions; process the sampled one or more latent variables with a decoder to obtain the reconstructed object; obtain a logarithm of probability that the sampled one or more latent variables have a defined property; compute entropy of the obtained latent variable distributions; compute logarithm of the logarithm of probability to obtain an obtained logarithm probability; subtract the obtained logarithm probability from the entropy to obtain an approximation of the Kullback-Leibler divergence; subtract approximation of the Kullback-Leibler divergence from the logarithm of probability; and obtain an estimated lower bound objective for variational interference. In some aspect, the method can further include: first, computing a mean of all estimated lower bound objectives on all objects of the dataset; and second, performing the gradient descent.

In some embodiments, the methods can include: defining one or more conditions for the objects; and allowing one or more undefined conditions for the objects to have arbitrary initial values.

In some embodiments, the computing of the probability of the samples having the defined object properties includes: computing probability of object properties for the object with a tensor train distribution; computing probability of both object properties and the latent code with a tensor train distribution; and computing probability of the latent code conditioned on object properties by conditional probability formula.

In some embodiments, the computing probability of both object properties and the latent code with a tensor train distribution includes: set a buffer to eye matrix; determining whether an object property is discrete or continuous or undefined; when the object property is discrete, computing a dot product with onehot($y_j$) along middle index, wherein $y_j$ is the object property; when the object property is discrete, computing a dot product with $[N(y_j\ mu_i, std_i),$ for all i] along middle index, wherein $mu_i$ is a mean of i and $std_i$ is a standard deviation (e.g., sigma) of i, wherein i is an object; when the object property is discrete, computing a dot product with $(1, 1, \ldots, 1)$ along the middle index, from the obtained dot product, make the dot product with the buffer to obtain a new buffer; and compute trace of new buffer and set the trace as probability of $(y_1, \ldots, y_n)$.

In some embodiments, the trained model is further trained with reinforced leaning, wherein the reinforced learning produces the reconstructed objects having a defined characteristic. In some aspects, the training of the trained model with the reinforced learning includes: discarding the object encoder; fixing weights of all layers of the object decoder except for a first layer of the object decoder; performing the following steps until convergence: estimate a mean and variance for each dimension of a previously obtained distribution of latent variables, the previously obtained distribution of latent variables being defined as a learnable prior; obtain an exploration latent variable for each dimension from outside of the latent variables produced by the encoder; pass the exploration latent variable through a decoder to obtain a reconstructed object based on the exploration latent variable; compute rewards for the reconstructed object based on at least one defined reward; and apply a single gradient ascent step to maximize a total reward with respect to a parameter of the learned prior and first layer of the decoder.

In some aspects, when the object is a molecule, the reward includes: a general biological activity self-organizing Kohonen map which provides a reward for reconstructed objects that are molecules with a biological activity in a biological pathway; a specific biological activity self-organizing Kohonen map which provides a reward for reconstructed objects that are molecules with a biological activity with a specific biological substance; and a trend self-organizing Kohonen map which provides a reward for reconstructed objects that are molecules with chemical moieties that devolved within a defined timeframe. In some aspects, the general biological activity self-organizing Kohonen map which provides a reward for reconstructed objects that are molecules with a biological activity in a kinase biological pathway. In some aspects, a specific biological activity self-organizing Kohonen map which provides a reward for reconstructed objects that are molecules with a biological activity with a DDR1 protein. In some aspects, a trend self-organizing Kohonen map which provides a reward for reconstructed objects that are molecules with chemical moieties that devolved within a defined timeframe.

In one embodiment, a method of generating an object with a desired property can include: obtaining the trained model of one of the embodiments; identify a desired object property; obtaining a latent code from a tensor train distribution conditioned on the desired object property; generating the object with the desired object property with the decoder; and providing the generated object with the desired object property. In some aspects, the method can include obtaining a plurality of generated objects with the desired object property; filtering the plurality of generated objects based on one or more parameters; and selecting one or more generated objects based on the filtering.

In some embodiments, a method of obtaining a physical form of the object can include: selecting a selected generated object; obtaining a physical form of the selected generated object; and validating the physical form of the selected generated object. In some aspects, the method can include: selecting a provided generated object; obtaining a physical form of the selected generated object; and validating the physical form of the selected generated object.

In some embodiments, generating an object can include: obtaining a learnable prior based on the latent code and desired properties; obtaining a set of properties; marginalize the learnable prior and the set of properties over a set of desired properties not in the set of properties; conditioning the marginalized learnable prior over properties in the set of properties to obtain a distribution over latent space; sampling the distribution over latent space; and processing the sampled distribution over latent space with a decoder to obtain a generated object with predefined properties.

In some embodiments, a computer program product includes a non-transient, tangible memory device having computer-executable instructions that when executed by a processor, cause performance of a method comprising: providing a model configured as a variational autoencoder with a learnable prior, which is parameterized with a tensor train, providing a dataset having object data for an object and condition data for a condition, wherein the condition may be a property of the object; processing the object data of the dataset to obtain latent object data with an object encoder of the model, wherein the latent object data includes a distribution of latent variables having a mean and a variance; sampling one or more latent variables from the obtained distribution of latent variables; processing the sampled one or more latent variables with defined object properties to compute a probability of the samples having the defined object properties; processing the samples one or more latent variables through an object decoder to obtain a reconstructed object; determining a reconstruction loss of the reconstructed object from an original object from the object data; computing a Kullback-Leibler divergence from the probability of the samples having the defined object properties; using the determined reconstruction loss and computed Kullback-Leibler divergence to compute a loss from the data set; perform a gradient descent until the reconstructed object is sufficiently representative of the original object and has the defined object properties; obtaining a trained model configured as a trained variational autoencoder with a learnable prior that is parameterized with a tensor train; and providing the trained model.

In some embodiments of the computer program product, the executed method further comprises further training the trained model with reinforced leaning, wherein the reinforced learning produces the reconstructed objects having a defined characteristic, wherein the training of the trained model with the reinforced learning includes: discarding the object encoder; fixing weights of all layers of the object decoder except for a first layer of the object decoder; performing the following steps until convergence: estimate a mean and variance for each dimension of a previously obtained distribution of latent variables, the previously obtained distribution of latent variables being defined as a learnable prior; obtain an exploration latent variable for each dimension from outside of the latent variables produced by the encoder; pass the exploration latent variable through a decoder to obtain a reconstructed object based on the exploration latent variable; compute rewards for the reconstructed object based on at least one defined reward; and apply a single gradient ascent step to maximize a total reward with respect to a parameter of the learned prior and first layer of the decoder.

In one embodiment, the imposed condition of a VAE-TTLP is fulfilled by the generated object (e.g., product) being as complex as the object itself. The DNN architecture can be used for the generation of specific molecules (e.g., generated object or product) having a desired action on human cells or certain physical properties (e.g., condition or property), or one or more molecules (e.g., generated object or product) that bind to a target protein or have a certain physical structure (e.g., condition or property). Those problems are common in the field of drug discovery. In both cases, the condition (a protein, or a cell state before receiving a molecule and a cell state after receiving the molecule) or property (solubility, molecular weight, 3D conformation) is at least as complex as the object (a candidate molecule for a drug) itself.

In an example, the output of the object encoder is analyzed for a specific distribution. For example, the distribution of the object information (e.g., latent object data) should be a standard normal distribution. For example, all the molecules (e.g., object data) are processed through the object encoder to get the latent object data, which includes generated molecules that are distributed as a standard deviation (e.g., sigma) distribution. The Tensor Train performs the data processing in order to determine if the generated molecule data (e.g., latent object data) are within a standard deviation (e.g., sigma) distribution of the object data.

In some embodiments, the molecules of the generated object data from the decoder are analyzed, and one or more specific molecules that fit the condition criteria are selected. The selected one or more molecules are then selected and synthesized before being tested with one or more cells to determine whether or not the synthesized molecules actually satisfy the condition 104.

In some embodiments, the VAE-TTLP architecture is a computer model that can be implemented in a computer or computing system. The model is configured to generate a molecule with a desired properties. Once one or more molecules are generated, the model can categorize the molecules according to whatever profile is desirable. A specific physical property, such as certain chemical moieties or 3D structure can be prioritized, and then a molecule with a profile that matches the desired profile is selected and synthesized. As such, an object selector (e.g., molecule selector), which can be a software module, selects at least one molecule for synthesis, which can be done by filtering as described herein. The selected molecule is then provided to an object synthesizer, where the selected object (e.g., selected molecule) is then synthesized. The synthesized object (e.g., molecule) is then provided to the object validator (e.g., molecule validator, which tests the object to see if it satisfies the condition or property, or to see if it is biologically active for a specific use. For example, a synthesized object that is a molecule can be tested with live cell cultures or other validation techniques in order to validate that the synthesized molecule satisfies the desired property.

The method can include comparing the generated object data with the object data with an object losses module. During such a comparison, losses from the object data to the generated object data can be calculated. The calculated losses can be compared to a losses threshold. Then, a generated object of the generated object data can be selected such as with an object selector, wherein the selected object is a generated object that is less than the threshold. This can include selecting a selected generated object data that is less than a threshold object difference between the generated object data and the object data.

Once a generated object is selected, then the method includes validating the selected object. The validation can be performed as described herein. When the object is a molecule, the validation can include synthesis and then testing with live cells.

Figure 4B:
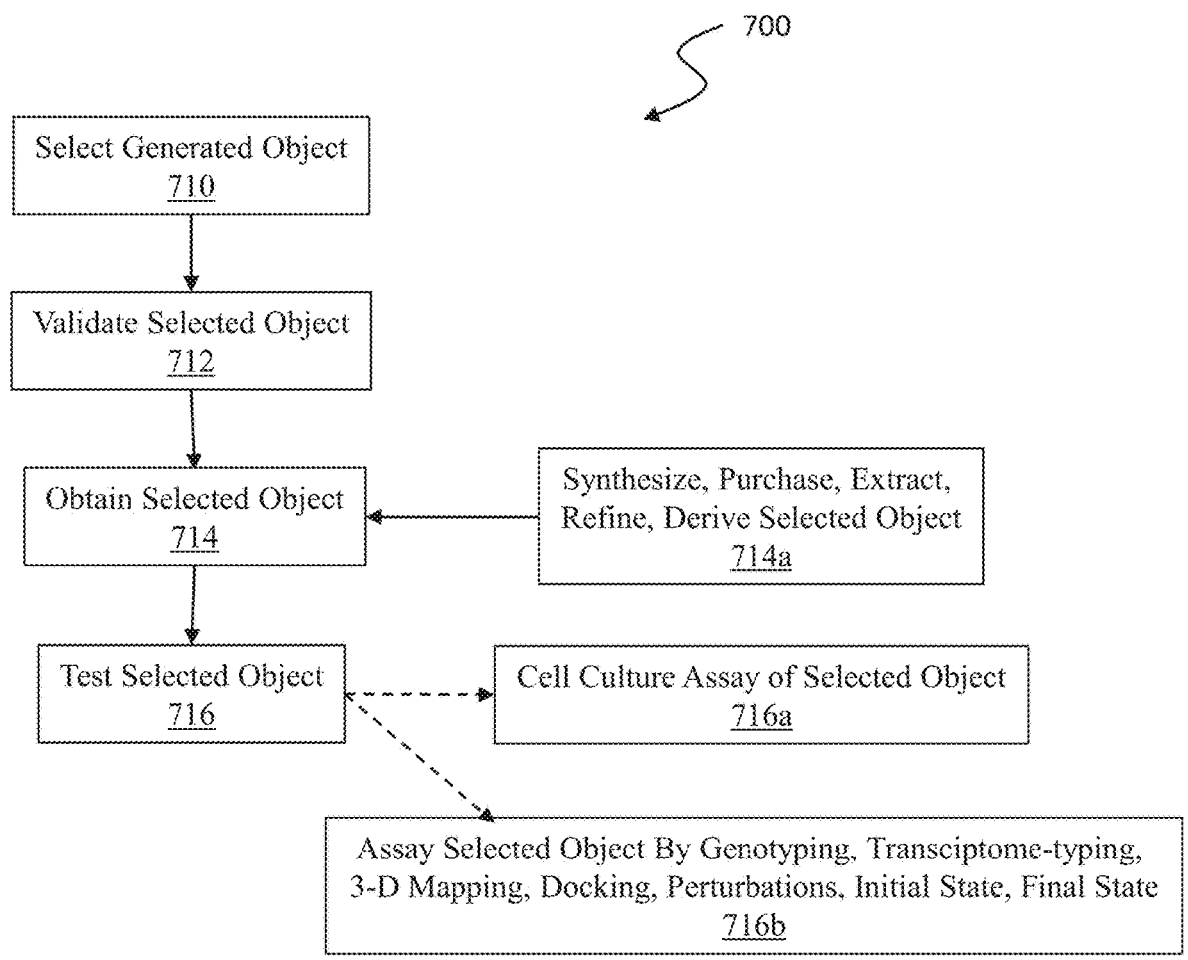
FIG. 4B includes a flowchart describing the validation and testing of the generated object from the VAE-TTLP model.

In some embodiments, a method 700 can include selecting a selected object 710 that corresponds with the selected generated object data or that corresponds with the desired properties; and validating the selected object 712 as shown in FIG. 4B. In some embodiments, the method 700 may include: obtaining a physical object for the selected object 714; and testing the physical object to have a desired property or biological activity 716), as shown in FIG. 4B. Also, in any method the obtaining of the physical object can include at least one of synthesizing, purchasing, extracting, refining, deriving, or otherwise obtaining the physical object (714*a*). The physical object may be a molecule or other. The methods may include the testing involving assaying the physical object in a cell culture (716*a*). The methods may also include assaying the physical object by genotyping, transcriptome-typing, 3-D mapping, ligand-receptor docking, before and after perturbations, initial state analysis, final state analysis, or combinations thereof (716*b*). Preparing the physical object for the selected generated object can often include synthesis when the physical object is a new molecular entity. Accordingly, the methods may include selecting a generated object that is not part of the original dataset or previously known.

When the DNN-based methods described herein are used for tasks, such as new molecule design and molecular feature extraction, drug-like molecular structure can be represented using a string, such as in formats like SMILES (simplified molecular-input line-entry system).

The decoders, such as the object decoder, use the latent representations produced by the object encoder. The object decoder attempts to reconstruct the original object using the latent representation of the object (latent object data) given the desired property.

Another part of the model can include a discriminator. This discriminator can serve as a regularizer for the distribution of latent representations (e.g., distributions of latent object data). The discriminator makes the conditional distribution of the latent object data similar to some predefined prior distribution, e.g. the standard normal distribution of the object data.

In one embodiment, the architecture can be a single algorithm (e.g., model) or each component may be a separate algorithm. The input for the algorithm is a dataset of data pairs containing representations of an object (e.g., object data) and a property (e.g., property data). In an example, the object is a molecule represented as a string in a SMILES format.

The VAE-TTLP model can be trained with training datasets in order to be capable of performing the operations described herein. The training procedure includes two steps executed alternately: (1) a generator step; and (2) a discriminator step. A separate objective function is optimized for one optimization step at each update using an optimization method. An Adam optimizer is an example. Training is terminated when the model loss converges or a maximum number of iterations is reached, which can be defined. As such, the iterations can be used to train the neural networks with the training datasets. A result of this training procedure is a generative model, which is capable of producing new objects (e.g., new molecules) approximately matching specified conditions (e.g., desired physical property and/or specific biological activity).

Figure 7:
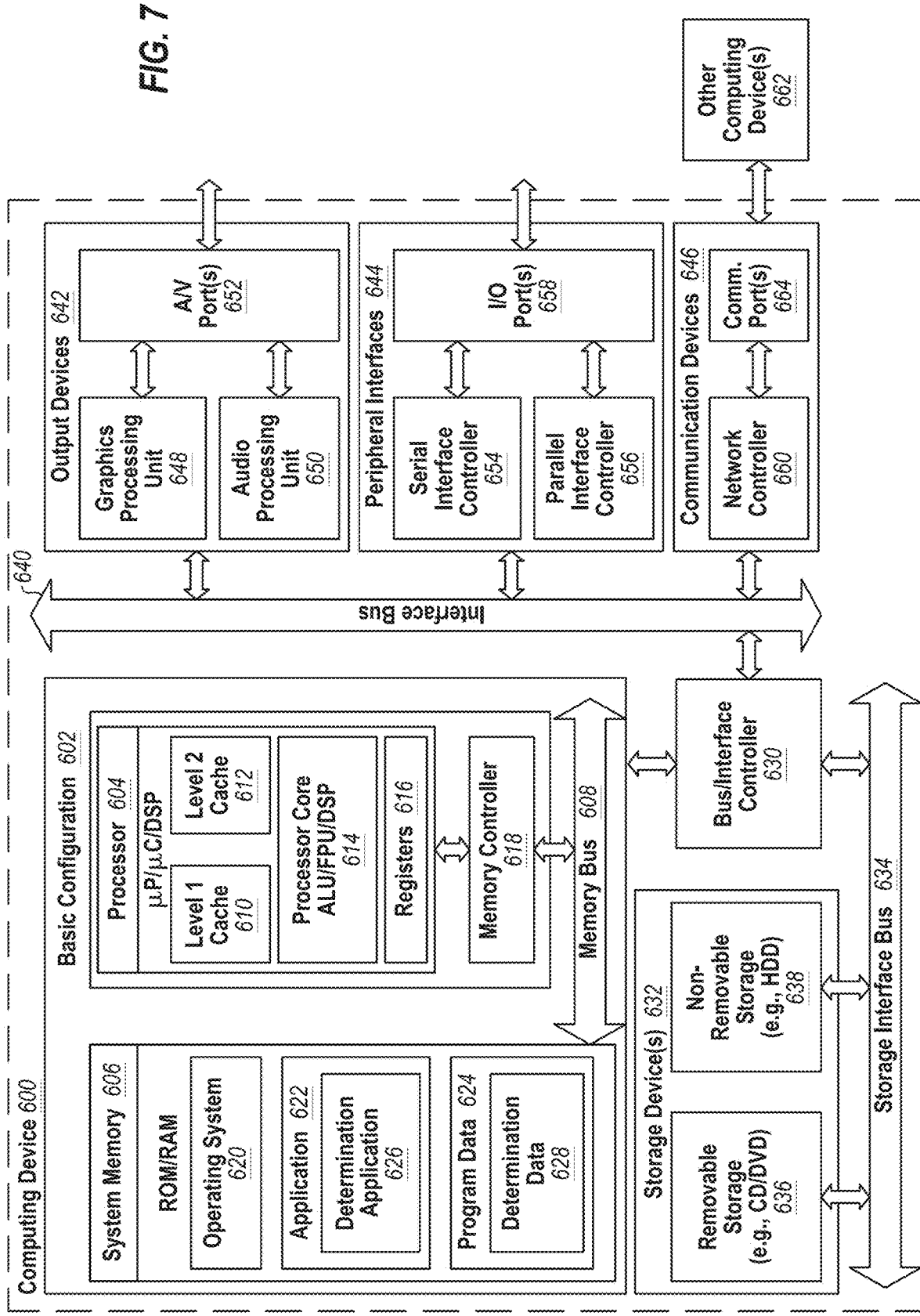
FIG. 7 illustrates an embodiment of a computing device.

The methodologies provided herein can be performed on a computer or in any computing system, such as exemplified in FIG. 7.

In some embodiments, the method can include: comparing the generated object data with the object data; and selecting a selected generated object data that is less than a threshold object difference between the generated object data and the object data.

In some embodiments, the method can include: selecting the selected object that corresponds with the selected generated object data or that corresponds with the selected generated condition data.

In some embodiments, the method can include: preparing the physical form of the selected object; and testing the physical object with the condition.

In some embodiments, the method can include: the obtaining of the physical form of the selected object includes at least one of synthesizing, purchasing, extracting, refining, deriving, or otherwise obtaining the physical object; and/or the testing includes assaying the physical form of the selected object in a cell culture; and/or assaying the physical form of the selected object by genotyping, transcriptome-typing, 3-D mapping, ligand-receptor docking, before and after perturbations, initial state analysis, final state analysis, or combinations thereof.

In some embodiments, the method can include determining whether the molecule satisfies the condition by having a desired property, such as a specific biological activity.

In some embodiments, the method can include determining the molecule is similar to one or more molecules in the object data; and determining the molecule has an activity similar to the one or more molecules in the condition/property data.

In some embodiments, the method can include: determining the molecule is distinct from other molecules with other mechanisms of action.

In some embodiments, the dataset includes data for molecule-protein binding. In some aspects, the method can include configuring an object decoder that generates molecules that bind with a given protein.

The VAE-TTLP model can be used to solve a subset conditioning problem, using only partially specified condition values. The Tensor Train format allows the VAE-TTLP model to capture complex underlying dependencies between latent codes and labels. VAE-TTLP can be used as a discriminative model to predict missing/unobserved values and can be trained from any auto-encoding encoder/decoder pair. As shown in the experiments, VAE-TTLP provides diverse samples satisfying specified conditions and can be used for the task of generating new objects with some of the conditions being unknown during the training or generation procedures.

EXAMPLES

Experimental evaluation of the VAE-TTLP model on two image datasets: MNIST and CelebA. Both datasets have attributes which can be used for conditional learning and generation. MNIST has a categorical class label feature, and for CelebA images we selected 10 binary attributes, including gender, hair color, smile, eyeglasses, and the like.

The protocol used an 8-layer neural network convolutional neural network with 6 convolutional and 2 fully-connected layers for the encoder and a symmetric architecture with deconvolutions for the decoder. MNIST samples are 28×28 gray-scale images. In CelebA, we worked with images in 64×64 resolution. CelebA faces were used to evaluate the model on generation of, conditioning images on a subset of attributes. Both of these datasets have attributes which were used for conditional learning and generation. The attributes can be both categorical (e.g., absence or presence mustaches on face, type of hairs: blond, black, etc.) and continuous (e.g., angle of face rotation, digit inline, line thickness).

Some objects can have some attributes that are missing (e.g., referred to as missings) in and some objects can have all attributes missing. The missings can take place because of cost/time load of computing attribute or can be specially missed because of possible error. This happens in molecular chemistry where computing some attribute of molecule is expensive. As a result, the VAE-TTLP can be used for generating objects, such as those described herein or known, where images and molecules are specific examples.

Figure 8:
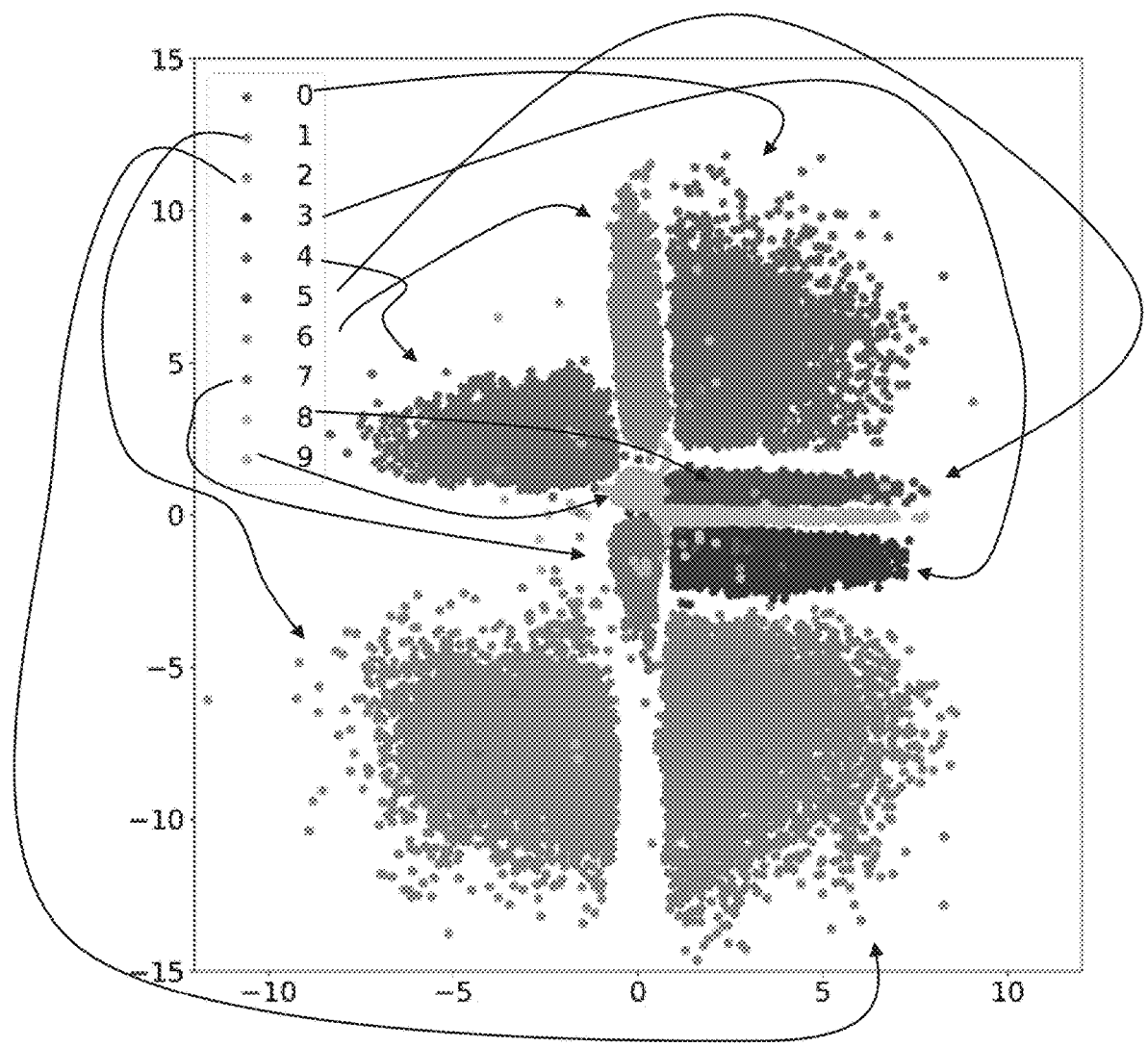
FIG. 8 shows the samples for the VAE-TTLP model trained on the MNIST database with the learned latent space being shown.
Figure 9:
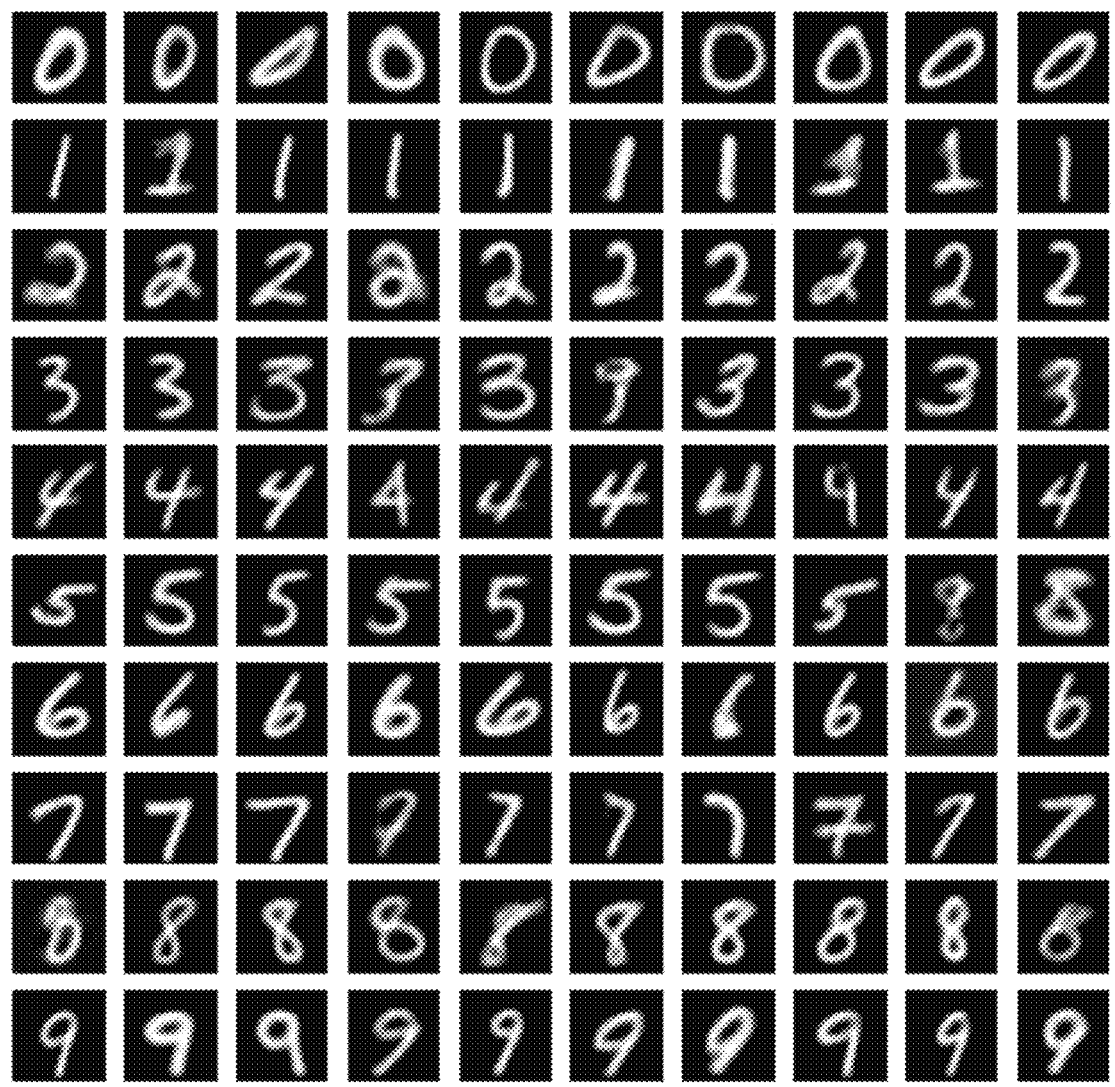
FIG. 9 shows the samples of digits obtained from processing the VAE-TTLP model.

For the first experiment, the protocol visualizes a latent space of a learned VAE-TTLP model trained on MNIST data for a model with a 2D latent space. In FIG. 8, it can be seen that the model assigned a separate cluster at the latent space for each label 0-9. The clusters for each label are shown by the arrows. FIG. 8 shows the samples for the VAE-TTLP model trained on the MNIST database with the learned latent space being shown. FIG. 9 shows the samples of digits obtained from processing the VAE-TTLP model.

The VAE-TTLP model was studied by visually and numerically comparing the quality of images generated with three models: CVAE (Conditional Variational Autoencoder—Sohn, Kihyuk, Honglak Lee, and Xinchen Yan. "Learning Structured Output Representation using Deep Conditional Generative Models." Advances in Neural Information Processing Systems. 2015.), VAE-TTLP and VAE-TTLP with a pretrained VAE on the CelebA dataset. To estimate the visual quality of samples, the protocol calculates a Fréchet Inception Distance (FID) that is shown to correlate with an assessor's opinion. To estimate how well a generated image matches a specified condition, the protocol can predict images' attributes with a separately trained predictor. Results are shown in Table 1 along with samples for visual analysis. The data showed the VAE-TTLP being superior for creating clear images. These experiments suggest that VAE-TTLP outperforms or gives comparable results to CVAE in both visual quality and condition matching.

Also, the pretrained VAE-TTLP model performs reasonably well, indicating that the model can be pretrained on unlabeled datasets.

TABLE 1

Numerical comparison of generated images from different models.

| Model | MNIST | | CelebA | |
| --- | --- | --- | --- | --- |
| | FID | Accuracy, % | FID | Accuracy, % |
| CVAE | 39.10 | 86.34 | 220.53 | 82.89 |
| VAE-TTLP | 40.80 | 89.94 | 165.33 | 88.79 |
| VAE-TTLP (pretrained VAE) | 47.53 | 75.39 | 162.73 | 87.5 |

The performance of the VAE-TTLP model for different levels of missing data as analyzed: fully labeled data and data with 30% and 70% randomly missing attributes. During the generation, the model was conditioned on a full set of attributes. Numerical results are reported in Table 2. As seen in the results, the model is quite stable even when the dataset is sparsely labeled. This shows the improvement of the VAE-TTLP model and protocol of use.

TABLE 2

Performance of VAE-TTLP on dataset with different percentage of missing attributes.

| Missing attributes, % | MNIST | | CelebA | |
| --- | --- | --- | --- | --- |
| | FID | Accuracy, % | FID | Accuracy, % |
| 0 | 40.80 | 89.94 | 165.33 | 88.7 |
| 30 | 41.33 | 89.84 | 178.32 | 84.89 |
| 70 | 41.86 | 88.97 | 169.10 | 87.08 |

The VAE-TTLP model can be used for imputing missing conditions by sampling from distribution $p_\psi(y|x)$. On the MNIST dataset, the VAE-TTLP model resulted in 95.4% accuracy and 89.21% accuracy on CelebA.

Figure 10:
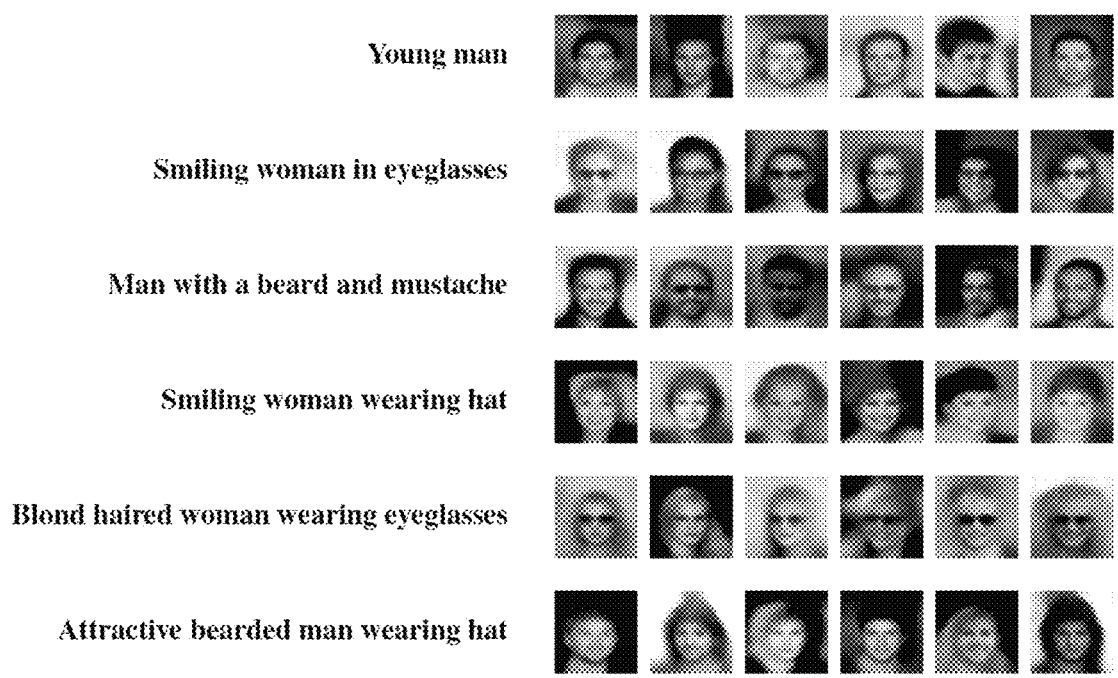
FIG. 10 shows generated images that indicate the VAE-TTLP model learned to produce highly diverse images with multiple varying attributes.

The VAE-TTLP model was used to generate images given a subset of conditions to estimate diversity of generated images. For example, if the protocol specifies an image to generate 'Young man', it should generate different images to specify different hair colors, presence and absence of glasses and hat, or other attributes. The generated images shown in FIG. 10 indicate that the model learned to produce highly diverse images with multiple varying attributes. It should be noted that the generated images show high diversity for a given attribute, which can be seen by comparing images in the same row.

Figure 11:
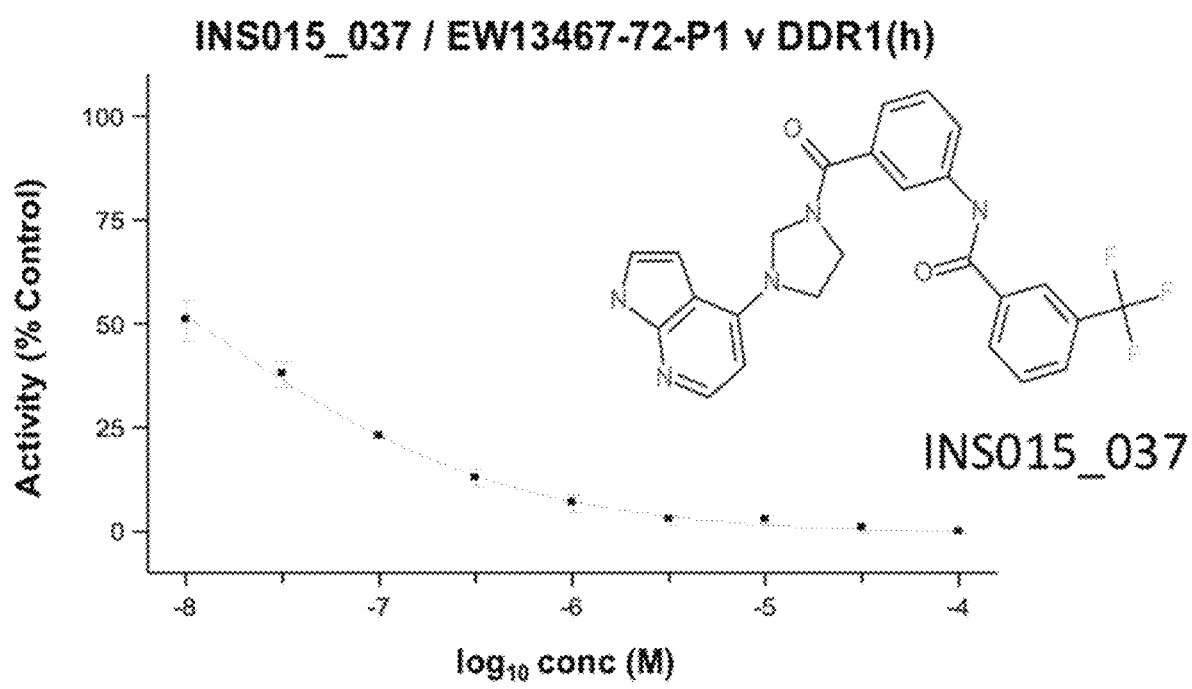
FIG. 11 shows a novel inhibitor of DDR1 kinase inset in a graph showing activity versus concentration.

While the foregoing examples used VAE-TTLP without RL, the following example shows the VAE-TTLP model with RL for chemical design. A VAE-TTLP model with RL as described above was used to generate a previously unknown inhibitor of DDR1 kinase (FIG. 11) with a nanomolar activity, proving that the model can generate novel molecular structures. To discover this molecule, the protocol generated 30,000 molecules from a VAE-TTLP model with RL, and selected 40 novel molecules by filtering them with a filtering pipeline described below.

Filtering Pipeline

The filtering pipeline can use the Pharmacophore Hypothesis, Non-Linear Sammon Mapping, and/or Molecular Generation and Selection Procedure.

Pharmacophore Hypothesis

On the basis of X-ray data available in PDB database (PDB codes: 3ZOS, 4BKJ, 4CKR, 5BVN, 5BVO, 5FDP, 5FDX, 6GWR), we have developed three pharmacophore models describing DDR1 inhibitors. In order to obtain the superposition of the ligands, 3D-alignment of the complexes was carried out. These 3-, 4- and 5-centered pharmacophore hypotheses include basic features responsible for binding to the active site of DDR1 kinase including: (1) hydrogen bond acceptor at the hinge region; (2) aromatic/hydrophobic linker; and (3) hydrophobic center in the pocket located in proximity to the DFG motif. This information can be used to select one or more molecules from those generated by the VAE-TTLP with or without RL. In most instances, it is used to narrow down generated molecules into a manageable number.

Nonlinear Sammon Mapping

To make the final selection of a designed molecule, we used a Sammon-based mapping technique. The main goal of this algorithm lies in the approximation of local geometric and topological relationships hidden in the input chemical space on a visually intelligible 2D- or 3D-dimensional plot. The fundamental idea of this methodology is to substantially reduce the high dimensionality of the initial dataset into the low-dimension feature space, and, in this aspect, it resembles a SOM approach and multidimensional scaling. However, in contrast to other algorithms, a classical Sammon-based method allows scientists to construct a projection, which reflects as global topographic relationships as pair-wise distances between all the objects within the whole space of input vector samples. Structures which successfully passed all the selection procedures described above were used as an input chemical space. For mapping, we used the same set of molecular descriptors which was applied for specific kinase SOM and added RMSD (root-mean-square deviation) values obtained during pharmacophore modeling as additional inputs. Euclidean distances were used as a similarity metric, stress threshold: 0.01, interaction number: 300, optimization step: 0.3, structural similarity factor: 0.5. The resulting map demonstrates that structures are normally distributed within the Sammon plot.

Molecule Generation and Selection Procedure

Using the VAE-TTLP model we generated 30,000 unique valid structures by sampling latent codes from the learned manifold $p_\psi(z)$ and sampling structures from the decoder distribution $p_\theta(x|z)$. To select the batch of molecules for synthesis and biological studies, we have developed a prioritization pipeline. At an initial step, the dataset was reduced to the size of 12,147 compounds using the following molecular descriptor thresholds: $-2<\log P<7$, $250<MW<750$, HBA+HBD<10, TPSA<150, NRB<10. After that, 150 MCFs (Medicinal Chemistry Filters) were applied to remove toxic and unstable structures. These include: potential substrates for 1,4-additions (Michael-bearing moieties) and other electrophilic species (e.g. para- or ortho-halogen substituted pyridines, 2-halogen substituted furans and thiophenes, alkyl halides, aldehydes and anhydrides, etc.), disulfides, isatins, barbiturates, strained heterocycles, fused polyaromatic systems, detergents, hydroxamic acids and diazo-compounds, peroxides, unstable fragments as well as sulfonyl ester derivatives. In addition, we used more trivial filtering rules including the following: $<2NO_2$ groups, $<3Cl$, $<2Br$, $<6F$, $<5$ aromatic rings, undesired atoms, such as Si, Co or P, to reasonably reduce the number of structures spread within the entire chemical space to a more compact and drug-like biased set. This procedure resulted in 7912 structures. A clustering analysis was then performed based on Tanimoto similarity and standard Morgan fingerprints implemented in RDKit. All compounds that satisfied a 0.6 similarity threshold were assigned to one cluster, with a minimum value of 5 structures per cluster. Inside each cluster, the compounds were sorted according to internal dissimilarity coefficient to output top 5 molecules with the maximum diversity in structure. As the result, the dataset was reduced to 5542 molecules. Then, we performed a similarity search using vendors' collections (MolPort and ZINC) and additionally removed 900 compounds with similarity >0.5 to increase the novelty of generated structures. The General Kinase SOM and Specific Kinase SOM were used to prioritize the compounds by their potential activity against DDR1. Out of 2570 molecules classified as kinase inhibitors by General Kinase SOM, 1951 molecules were classified as DDR1 inhibitors by Specific Kinase SOM, which were used for pharmacophore screening. For every molecule, 10 conformations were generated and minimized using RDKit implementation of UFF (Universal Force Field). Using the derived hypothesis, a pharmacophore screening procedure was performed, which resulted in a set of RMSD values for 848 molecules matching at least one pharmacophore hypothesis. On the basis of Sammon Mapping, we have performed the random selection procedure placing special attention to the areas of RMSD values obtained for 4- and 5-centered pharmacophores. As a result, 40 molecules were selected for synthesis and subsequent biological evaluation.

For the models, and processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

FIG. 6 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and/or an experimental protocol for validating the molecule. Other executable instructions may also be provided.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A non-transitory computer-readable media comprising:
one or more non-transitory computer-readable media storing instructions that in response to being executed causes performance of operations, the operations comprising:
inputting a desired object property into a deep neural network;
obtaining, from a trained conditional generative model, a latent code from a tensor train-induced joint distribution conditioned on the desired object property, which is generated by an encoder of the deep neural network;
generating the object with the desired object property with a decoder of the deep neural network; and
providing the generated object with the desired object property.

2. The non-transitory computer-readable media of claim 1, the operations further comprising:
defining at least one desired property as a subset of properties used in training the trained conditional generative model;
marginalizing the learnable prior over one or more undesired properties that are not included in the at least one desired property;

conditioning the marginalized learnable prior over properties in a dataset to obtain a distribution over conditioned latent space having a high density area with objects with the at least one desired property;
sampling a latent variable from the conditioned latent space; and
generating the object with the at least one desired property.

3. The non-transitory computer-readable media of claim 1, wherein the object is selected from an image, video, audio, text, molecule, biological data profile, or combinations thereof.

4. The non-transitory computer-readable media of claim 3, wherein the object is a molecule.

5. The non-transitory computer-readable media of claim 4, wherein the property is selected from biological profile, binding with a target protein, biological activity, pharmacokinetics, absorption, distribution, metabolism, excretion, toxicity, physicochemical property, solubility, molecular weight, 3D conformation, molecular weight, melting point, boiling point, vapor point, molecular polarity, Henry's phase distribution, at last one defined chemical moiety, and combinations thereof.

6. The non-transitory The computer-readable media of claim 1, the operations further comprising:
obtaining a learnable prior based on the latent code and desired properties;
obtaining a set of properties;
marginalize the learnable prior and the set of properties over a set of desired properties not in a set of the at least one desired property;
conditioning the marginalized learnable prior over properties in the set of properties to obtain a distribution over latent space;
sampling the distribution over latent space; and
processing the sampled distribution over latent space with a decoder to obtain the generated object with predefined properties.

7. The non-transitory computer-readable media of claim 4, further comprising using a molecule selector module to select at least one molecule by filtering for the desired object property.

8. The non-transitory computer-readable media of claim 7, wherein the filtering removes molecules that are toxic or unstable.

9. The non-transitory computer-readable media of claim 7, wherein the filtering removes molecules having identified moieties, having a number of a moiety higher than a threshold, and/or undesirable atoms.

10. The non-transitory computer-readable media of claim 4, the operations further comprising:
performing a clustering analysis and grouping a plurality of molecule structures per cluster; and
performing a similarity search on the plurality of molecule structures and removing molecule structures below a threshold.

11. The non-transitory computer-readable media of claim 4, the operations further comprising prioritizing molecules having a defined biological activity.

12. The non-transitory computer-readable media of claim 1, the operations comprising:
comparing generated object data with input object data;
calculating losses from the input data to the generated object data;
comparing the losses to a losses threshold; and
selecting an object having a loss less than the losses threshold.

13. The non-transitory computer-readable media of claim 1, wherein the operations comprise training a variational autoencoder with a learnable prior to obtain the trained conditional generative mode which is performed on a computing system with a deep neural network having a conditional generative model configured as a variational autoencoder with a learnable prior, wherein the learnable prior is a complex distribution parameterized by a tensor train decomposition, wherein the conditional generative model is configured for solving a subset conditioning problem by estimating a joint distribution of latent codes and conditions for a respective object in a tensor train format, the training comprising:
providing a dataset to the conditional generative model, the dataset having object data for a plurality of objects and property data for a property of a first portion of the plurality of objects and without the property data for a second portion of the plurality of objects, wherein the property is a defined object property;
processing the object data of the dataset with an object encoder of the conditional generative model to obtain latent object data from the object data mapped onto the prior distribution, wherein the latent object data includes a distribution of latent variables having a mean and a variance, wherein the latent object data is based at least partially on the property data;
sampling one or more latent variables from the obtained distribution of latent variables with the conditional generative model, wherein the sampled one or more latent variables are based at least partially on the property data;
processing the sampled one or more latent variables with the tensor train decomposition of the conditional generative model, wherein the processing is performed with the defined object property in order to compute a probability of the samples having the defined object property;
processing the sampled one or more latent variables through an object decoder of the conditional generative model to obtain a reconstructed object;
determining a reconstruction loss of the reconstructed object from an original object from the object data with the conditional generative model;
computing a Kullback-Leibler divergence of the distribution of the latent variables from a distribution of the tensor train decomposition with the conditional generative model;
using the determined reconstruction loss and computed Kullback-Leibler divergence to compute a loss with the conditional generative model from the data set;
performing a gradient descent with the conditional generative model until the reconstructed object is sufficiently representative of the original object and has the defined object property;
obtaining a trained model configured as a trained variational autoencoder with the learnable prior, wherein the learnable prior parameterized by the tensor train decomposition; and
providing the trained conditional generative model.

14. The non-transitory computer-readable media of claim 1, wherein the operations comprise training a variational autoencoder with a learnable prior to obtain the trained conditional generative model with reinforced leaning, wherein the reinforced learning produces the reconstructed objects having the defined object property, wherein the training of the trained model with the reinforced reinforcement learning includes:

discarding the object encoder;

fixing weights of all layers of the object decoder except for a first layer of the object decoder;

performing the following steps until convergence:

estimate a mean and variance for each dimension of a previously obtained distribution of latent variables, the previously obtained distribution of latent variables being defined as a learnable prior;

obtain sample an exploration latent variable from outside of a manifold having the latent object data for each dimension from outside of the latent variables produced by learnable prior;

pass the exploration latent variable through the decoder to obtain a reconstructed object based on the exploration latent variable;

compute rewards for the reconstructed object based on at least one defined reward, wherein the at least one defined reward is for the reconstructed object to have the defined object property;

apply a single gradient ascent step to maximize a total reward with respect to parameters of the learned prior and first layer of the decoder; and obtaining a reinforced trained model.

15. A method of preparing a physical form of an object, comprising:

providing the non-transitory computer-readable media of claim 1;

obtaining generated object data of the generated object with the desired object property from performing the operations;

obtaining a physical form of the generated object; and validating the physical form of the generated object to have the desired object property.

16. The method of claim 15, wherein the object is selected from an image, video, audio, text, molecule, biological data profile, or combinations thereof.

17. The method of claim 16, wherein the object is a molecule.

18. The method of claim 17, wherein the property is selected from biological profile, binding with a target protein, biological activity, pharmacokinetics, absorption, distribution, metabolism, excretion, toxicity, physicochemical property, solubility, molecular weight, 3D conformation, molecular weight, melting point, boiling point, vapor point, molecular polarity, Henry's phase distribution, at last one defined chemical moiety, and combinations thereof.

19. The method of claim 15, comprising obtaining the physical form of the generated object by at least one of synthesizing, purchasing, extracting, refining, or deriving.

20. The method of claim 15, wherein the validating is by assaying the physical form of the generated object by genotyping, transcriptome-typing, 3-D mapping, ligand-receptor docking, before and after perturbations, initial state analysis, final state analysis, or combinations thereof.

* * * * *